(12) United States Patent
Libsch et al.

(10) Patent No.: US 11,016,048 B2
(45) Date of Patent: May 25, 2021

(54) MICRO-CAPACITANCE SENSOR ARRAY CONTAINING SPACED APART FIRST AND SECOND OVERLAPPING AND PARALLEL ELECTRODE PLATES FOR SENSING ANALYTES

(71) Applicant: International Business Machines Corporation, Armonk, NY (US)

(72) Inventors: Frank R. Libsch, White Plains, NY (US); Venkat K. Balagurusamy, Suffern, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/719,140

(22) Filed: Dec. 18, 2019

(65) Prior Publication Data

US 2020/0124557 A1    Apr. 23, 2020

Related U.S. Application Data

(62) Division of application No. 15/852,028, filed on Dec. 22, 2017, now Pat. No. 10,830,724.

(51) Int. Cl.
*G01N 27/22* (2006.01)
*G01N 33/543* (2006.01)
(Continued)

(52) U.S. Cl.
CPC ............. *G01N 27/22* (2013.01); *G01N 27/00* (2013.01); *G01N 33/5438* (2013.01); *G01N 33/5308* (2013.01)

(58) Field of Classification Search
CPC ........... G01N 33/5438; G01N 33/5091; G01N 33/54366; G01N 27/221; G01N 2033/4975; G01N 27/02; G01N 27/026; G01N 27/12; G01N 33/497; G01N 15/06; G01N 15/1484; G01N 21/6452; G01N 21/8483; G01N 2560/00; G01N 33/18; G01N 33/1826; G01N 33/487; G01N 33/49; G01N 33/4925; G01N 33/5005; G01N 33/5079; G01N 33/5094; G01N 33/54306;
(Continued)

(56) References Cited

U.S. PATENT DOCUMENTS

| | | |
|---|---|---|
| 4,920,047 A | 4/1990 | Giaever et al. |
| 5,164,319 A | 11/1992 | Hafeman et al. |

(Continued)

OTHER PUBLICATIONS

Führer T. et al., "An Integrated Source/Mask/DSA Optimization Approach", Proc. of SPIE 9780:97800M-1-97800M-12 (Mar. 23, 2016).

(Continued)

*Primary Examiner* — Vinh P Nguyen
(74) *Attorney, Agent, or Firm* — Scully, Scott, Murphy & Presser, P.C.; Daniel P. Morris, Esq.

(57) ABSTRACT

The present application provides devices, systems and methods for detecting the presence and/or length of an analyte. More specifically, the present application is directed to a structure and system that includes a micro-capacitive sensor array for detecting the presence of an analyte in a sample and determining the length and/or composition of an analyte, such as a nucleic acid, as well as methods for using the same.

15 Claims, 11 Drawing Sheets

(51) Int. Cl.
*G01N 27/00* (2006.01)
*G01N 33/53* (2006.01)

(58) Field of Classification Search
CPC ....... G01N 33/54346; G01N 33/54373; G01N 33/54393; G01N 33/581; G01N 33/587; G01N 33/66; G01N 33/6848; G01N 33/84; G01N 27/22; G01N 27/227; G01N 27/00; G01N 33/5308; B01J 19/0046; B01J 2219/00653; B01J 2219/0074; B01J 2219/00596; B01J 2219/00608; B01J 2219/00702; G01F 1/584; G06F 3/147
See application file for complete search history.

(56) References Cited

U.S. PATENT DOCUMENTS

| | | | |
|---|---|---|---|
| 5,270,664 A | 12/1993 | McMurtry et al. | |
| 6,317,508 B1 | 11/2001 | Kramer et al. | |
| 6,454,924 B2 | 9/2002 | Jedrzejewski et al. | |
| 7,217,562 B2 | 5/2007 | Cao et al. | |
| 7,435,384 B2 * | 10/2008 | Fish | G01N 33/54313 422/81 |
| 8,143,908 B2 | 3/2012 | Uenluebayir et al. | |
| 8,145,434 B2 * | 3/2012 | Shachar | G01N 33/54373 702/19 |
| 8,321,174 B1 | 11/2012 | Moyal et al. | |
| 8,783,466 B2 | 7/2014 | Han et al. | |
| 8,856,693 B2 | 10/2014 | Cheng et al. | |
| 8,882,980 B2 | 11/2014 | Ling et al. | |
| 9,110,055 B2 | 8/2015 | Cai et al. | |
| 9,111,067 B2 | 8/2015 | Robles | |
| 9,310,363 B2 | 4/2016 | Shachar et al. | |
| 9,821,310 B2 * | 11/2017 | Guldiken | B01L 3/502761 |
| 10,386,327 B2 * | 8/2019 | Shachar | G01N 27/4145 |
| 10,422,672 B1 * | 9/2019 | Libsch | G01N 15/1031 |
| 10,830,724 B2 * | 11/2020 | Libsch | G01N 33/5438 |
| 2005/0136419 A1 | 6/2005 | Lee | |
| 2008/0121045 A1 | 5/2008 | Cole et al. | |
| 2010/0262375 A1 | 10/2010 | Shachar et al. | |
| 2014/0008307 A1 | 1/2014 | Guldiken et al. | |
| 2015/0184235 A1 | 7/2015 | Reda et al. | |
| 2016/0144405 A1 | 5/2016 | Astier et al. | |
| 2016/0178999 A1 | 6/2016 | Wuister et al. | |
| 2016/0350465 A1 | 12/2016 | Guillorn et al. | |

OTHER PUBLICATIONS

Ruiz R. et al., "Line Roughness in Lamellae-Forming Block Copolymer Films", Macromolecules 50:1037-1046 (Jan. 27, 2017).

Tsai H. et al., "High Chi Block Copolymer DSA to Improve Pattern Quality for FinFET Device Fabrication", Proc. of SPIE 9779:977910-1-977910-7 (Mar. 25, 2016).

Wang C. et al., "Hydrodynamics of Diamond-Shaped Gradient Nanopillar Arrays for Effective DNA Translocation into Nanochannels", ACS Nano, Jan. 2015, pp. 1206-1218, 1206 9(2).

List of IBM Patents or Patent Applications Treated as Related Dated Dec. 18, 2019, 2 Pages.

Notice of Allowance dated Jul. 29, 2020 received in the parent U.S. Patent Application, namely U.S. Appl. No. 15/852,028, Copy Not Enclosed.

Office Action dated Apr. 6, 2020 received in the parent U.S. Patent Application, namely U.S. Appl. No. 15/852,028, Copy Not Enclosed.

* cited by examiner

P+/V+     PRESSURE OR VOLTAGE GRADIENT DRIVEN FLOW     P-/V-

MICRO-CAPACITANCE SENSOR ARRAY CONTAINING SPACED APART FIRST AND SECOND OVERLAPPING AND PARALLEL ELECTRODE PLATES FOR SENSING ANALYTES

FIELD OF THE DISCLOSURE

The present application relates to devices, systems and methods for detecting the presence and/or length of an analyte. More specifically, the present application is directed to a structure and system that includes a micro-capacitive sensor array for detecting the presence of an analyte in a sample and determining the length and/or composition of an analyte.

BACKGROUND

An antibody is a large multi-subunit protein that is used by the human immune system to neutralize pathogens such as, for example, a virus. The antibody recognizes a unique molecule of the pathogen, called an antigen. Each antibody contains a paratope (analogous to a lock) that is specific for one particular epitope (analogous to a key) on an antigen, allowing these two structures to bind together with precision. Using this binding mechanism, an antibody can tag a microbe or an infected cell for attack by other parts of the immune system, or can neutralize its target directly (for example, by blocking a part of a microbe that is essential for its invasion and survival). Depending on the antigen, the binding may impede the biological process causing the disease or may activate macrophages to destroy the foreign substance.

The most common immuno-absorbent methods like ELISA (i.e., enzyme-linked immunosorbent assay) and Western blot (sometimes referred to the protein immunoblot) are used to detect the binding of the antibodies to the viruses. But the detection is usually by optical means such as, for example, by using fluorescent markers. Since the number of antibodies that can bind to the viral surface is determined by the number of epitopes present on the viral surface, viral detection sets a serious limit to the amount of bound antibodies that can be detected. This makes detecting a small number of viruses by the prior art methods nearly impossible. There is thus a need for providing a highly sensitive structure for detecting the binding of antibodies to viruses.

Also, one of the primary goals of mapping nucleic acids such as DNA or RNA is to obtain information about the various disease related biomarkers in the nucleic acid. Currently such information is obtained by labeling DNA with appropriate fluorescent labels that will bind to the biomarker locations and imaging them with an optical microscope. However, optical imaging has an inherent positional resolution of 200 nm set by diffraction limit. This limit, in terms of the length of the DNA, translates to about 60 base pairs. There is thus also a need for providing a highly sensitive structure which is capable of providing information over more of the length of the DNA.

SUMMARY

In one aspect of the present disclosure, a micro-capacitive sensor array is provided. The micro-capacitive sensor array can include a first electrode plate containing at least one capacitive electrode that is geographically separated and electrically isolated from a second electrode plate that includes at least one conductive electrode. The first and second electrode plates are configured such that at least one channel for sensing an analyte is formed between the first electrode plate and the second electrode plate. In certain embodiments, the first electrode plate includes a plurality of first conductive electrodes having a first polarity that are spaced apart and electrically isolated from one another and the second electrode plate contains a single conductive electrode of a second polarity. In some embodiments, the first electrode plate and the second electrode plate are parallel. In other embodiments, one of the first electrode plate and the second electrode plate contains a plurality of electrodes that are geographically separated and electrically isolated from at least one set of the plurality of electrodes on the electrode plate to form at least two channels for sensing an analyte between the first electrode plate and the second electrode plate. In some embodiments, the micro-capacitive sensory array of the present disclosure includes at least one substrate. In specific embodiments, the micro-capacitive sensor array contains a first substrate including the first electrode plate and a second substrate that is parallel to the first substrate, which includes the second electrode plate. The micro-capacitive sensor array of the present disclosure can include at least one array of vertical pillars. In specific embodiments, the micro-capacitive sensor array includes an array of vertical pillars adjacent to the at least one channel for sensing an analyte. In some embodiments, the micro-capacitive sensor array includes a first array of vertical pillars adjacent to the at least one channel for sensing an analyte and a second array of vertical pillars adjacent to the at least one channel, such that the first array of vertical pillars and the second array of vertical pillars are located on opposite ends of the at least one channel for sensing an analyte. In certain embodiments, each vertical pillar in each of the least one array of vertical pillars has a first end contacting a first substrate and a second end contacting a second substrate. In other embodiments, the first substrate or the second substrate of the micro-capacitive sensor array includes an opening therein such that an analyte or a sample comprising an analyte can be provided. In some embodiments, the first substrate or the second substrate of the micro-capacitive sensor array includes an opening adjacent to a first end of the at least one channel such that an analyte or a sample comprising an analyte can be provided and a second opening adjacent to the opposite end of the at least one channel. In certain embodiments, each of the conductive electrodes on the first electrode plate includes a circuit for providing a first voltage or a first sequence of voltages relative to the voltage or sequence of voltages in other conductive electrodes on the first electrode plate forming an integrated sensing circuit. In certain embodiments, the micro-capacitive sensor array includes a processor connected to the integrated sensing circuit.

In another aspect of the present disclosure, a system for sensing an analyte is provided. The system includes a micro-capacitive sensor array of the present disclosure. The micro-capacitive sensor array includes a first electrode plate containing at least one capacitive electrode that is geographically separated and electrically isolated from a second electrode plate that includes at least one capacitive electrode. The first electrode plate and the second electrode plate are arranged such that at least one channel for sensing an analyte is formed between the first electrode plate and the second electrode plate. In certain embodiments, the first electrode plate includes a plurality of first conductive electrodes having a first polarity that are spaced apart and electrically isolated from one another and the second electrode plate contains a single conductive electrode of a second polarity. In some embodiments, the first electrode plate and the second electrode plate are parallel. In other embodiments, one of the first electrode plate and the second electrode plate contains a plurality of electrodes that are geographically separated and electrically isolated from at least one set of the plurality of electrodes on the electrode plate to form at least two channels for sensing an analyte between the first electrode plate and the second electrode plate. In some embodiments, the micro-capacitive sensory array of the present disclosure includes at least one substrate. In specific embodiments, the micro-capacitive sensor array contains a first substrate including the first electrode plate and a second substrate that is parallel to the first substrate, which includes the second electrode plate. In one embodiment, the micro-capacitive sensor array of the present disclosure includes at least one array of vertical pillars. In specific embodiments, the micro-capacitive sensor array includes an array of vertical pillars adjacent to the at least one channel for sensing an analyte. In some embodiments, the micro-capacitive sensor array includes a first array of vertical pillars adjacent to the at least one channel for sensing an analyte and a second array of vertical pillars adjacent to the at least one channel, such that the first array of vertical pillars and the second array of vertical pillars are located on opposite ends of the at least one channel for sensing an analyte. The system includes an integrated sensing circuit connected to the bottom electrode(s) and the top electrode(s) of the micro-capacitive sensor array for performing a time sequence of capacitance measurements in the milli- or nano-second time frame. The micro-capacitive sensor array can determine movement of an analyte by measuring the capacitance change between one or more electrodes on the first electrode plate and one or more electrodes on the second electrode plate. The system also includes a processor connected to the integrated sensing circuit for constructing an output such as a movement image of analyte or analytes. In certain embodiments, the processor provides a movement image that identifies the length of the analyte. In other embodiments, the processor provides an output that identifies the type of analyte detected in the micro-capacitive sensor array.

In yet another aspect of the present disclosure, a method for sensing an analyte is provided. The method includes providing a micro-capacitive sensor array. The micro-capacitive sensor array includes a first electrode plate containing at least one capacitive electrode that is geographically separated and electrically isolated from a second electrode plate that includes at least one electrode such that at least one channel for sensing an analyte is formed between the first electrode plate and the second electrode plate. In certain embodiments, the first electrode plate includes a plurality of first conductive electrodes having a first polarity that are spaced apart and electrically isolated from one another and the second electrode plate contains a single conductive electrode of a second polarity. In some embodiments, the first electrode plate and the second electrode plate are parallel. In other embodiments, one of the first electrode plate and the second electrode plate contains a plurality of electrodes that are geographically separated and electrically isolated from at least one set of the plurality of electrodes on the electrode plate to form at least two channels for sensing an analyte between the first electrode plate and the second electrode plate. In some embodiments, the micro-capacitive sensory array of the present disclosure includes at least one substrate. In specific embodiments, the micro-capacitive sensor array contains a first substrate including the first electrode plate and a second substrate that is parallel to the first substrate, which includes the second electrode plate. In one embodiment, the micro-capacitive sensor array of the present disclosure includes at least one array of vertical pillars. In specific embodiments, the micro-capacitive sensor array includes an array of vertical pillars adjacent to the at least one channel for sensing an analyte. In some embodiments, the micro-capacitive sensor array includes a first array of vertical pillars adjacent to the at least one channel for sensing an analyte and second array of vertical pillars adjacent to the at least one channel, such that the first array of vertical pillars and second array of vertical pillars are located on opposite ends of the at least one channel for sensing an analyte. Analytes or a sample comprising analytes is provided to the channel through an opening. In some embodiments, the analyte flows through the opening and enters a channel for sensing an analyte. In certain embodiments, the analyte provided traverses the opening to contact one or more pillars of an array of vertical pillars adjacent to a channel for sensing an analyte. In some embodiments, the analyte or a solution comprising an analyte traverses the channel when a pressure gradient is created at one end of the at least one channel for sensing an analyte or a voltage gradient is provided between opposing ends of the channel. Next, the analyte traverses a channel and the differential capacitances are measured between the bottom electrode(s) and the top electrode(s) of the micro-capacitive sensor array to determine movement of an analyte through the channel.

DETAILED DESCRIPTION

Figure 1A:
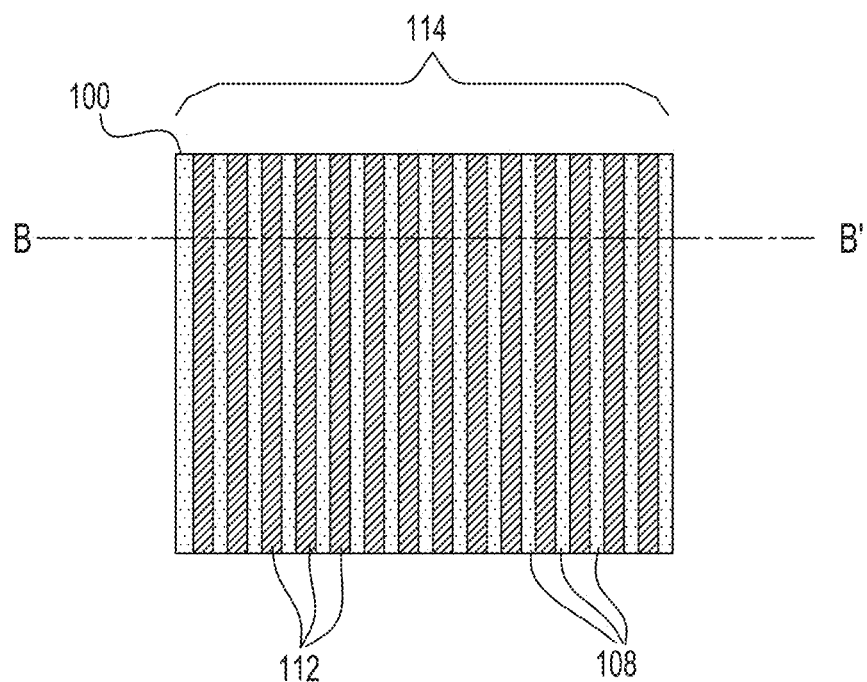
FIG. 1A is a top view of a first exemplary electrode plate that can be employed in the structures, systems and methods of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present.

FIGS. 1A-1F illustrate exemplary electrode plates 100 that can be employed in the micro-capacitance sensor arrays of the present disclosure. FIGS. 1A-1F depict exemplary electrode plate(s) 100 including at least one conductive electrodes 112 formed on, or embedded in the electrode plate 100. Here, each of the at least one conductive electrodes 112 of the electrode plate 100 is contacted by at least one surface of the electrode plate 100.

The electrode plate 100 may be rigid or flexible and can be comprised of a dielectric material. Exemplary dielectric materials that can be employed in an electrode plate 100 include, but are not limited to, silicon dioxide, silicon nitride, or a low dielectric constant (low-k) material such as organosilicate glass; the term "low-k denotes a dielectric material having a dielectric constant of less than silicon dioxide. The electrode plate 100 can be formed, for example, by CVD, PECVD or spin coating. The electrode plate 100 is optional and can be omitted in some embodiments of the present application, such as those set forth in FIGS. 1G-1I.

The at least one conductive electrode 112 can be any number, size and/or shape. For example, the conductive electrodes 112 can be a plurality of conductive lines that are spaced apart by a trench (space) 108 and electrically isolated from each other as shown in FIGS. 1A, 1C, 1E-1G and 1I. The conductive electrodes 112 can be arranged in parallel or non-parallel configurations. These conductive electrodes 112 may have the same or different widths. In one embodiment, the width of the conductive electrode 112 can be from 1 nm to 1 cm. The conductive electrode(s) 112 can also have other widths that are above and/or below the range mentioned above. In certain embodiments, the width of the spaces 108 between the conductive electrodes 112 are between 1 nm and 100 nm, between 10 nm and 80 nm, between 20 nm and 70 nm, between 30 nm and 60 nm or between 40 nm and 50 nm. In specific embodiments, the width of the spaces 108 between conductive electrodes 112 is 50 nm or less. The spacing 108 between adjacent conductive electrodes 112 may be uniform (i.e. the same) or different. In one embodiment and as shown in FIGS. 1A, 1C and 1E-1F, the electrode plate 100 contains a plurality of conductive electrodes 112 forming parallel conductive lines extending along a first direction. In some embodiments, the electrode plate 100 contains a plurality of conductive electrodes 112 forming a plurality of parallel conductive lines extending along a second direction that is different from the first direction. In one embodiment, the first direction and the second direction may be substantially perpendicular to each other, for example, the first direction is the vertical direction (the "y" direction) and the second direction is the horizontal direction (herein referred to as "x" direction). In other variant embodiments, the first direction and the second direction may be non-perpendicular to each other.

In certain instances, the at least one conductive electrode 112 can be formed in trenches within the electrode plate 100. For example, the at least one conductive electrode 112 can be formed within the electrode plate 100 by conventional lithography, etching and deposition processes. More specifically, a photoresist layer may first be formed on the electrode plate 100 and exposed to light to form a desired pattern of openings therein. An anisotropic etch such as, for example, a reactive ion etch (RIE), may then be performed to form trenches in the electrode plate 100 using the patterned photoresist layer as an etch mask. The trenches can be filled with a conductive material such as, for example, a transparent conductive oxide, such as a tin oxide (e.g., indium tin oxide (ITO), fluorine doped oxide (FTO)), gold, silver, nickel, copper, tungsten, aluminum or alloys thereof to provide the desired number and distribution of conductive electrodes 112. The surface of the structure can be planarized using a planarization process such as, for example, chemical mechanical polishing (CMP). After planarization, the top surface(s) of the conductive electrode(s) 112 are coplanar with the top surface of the electrode plate 100. This can be seen, for example, in FIG. 6C.

In other instances, the conductive electrode(s) 112 are formed on the electrode plate 100 by blanket depositing a conductive material followed by lithographically etching the conductive material. For example, a conductive material may be first blanket deposited directly on the electrode plate 100 using a conventional deposition process such as, for example, chemical vapor deposition (CVD), physical vapor deposition (PVD), plasma-enhanced vapor deposition (PECVD), or atomic layer deposition (ALD). A photoresist layer may then be formed on the conductive material, and exposed to light to form openings therein. The exposed conductive material may then be removed using RIE, through the openings, to form the conductive electrode(s) 112 using the patterned photoresist layer as an etch mask. Subsequently, the patterned photoresist layer may be removed, for example, by ashing. Here, the topmost surface(s) of the conductive electrode(s) 112 are thus raised above the topmost surface of the electrode plate 100, as shown for example, in FIG. 6A.

In yet another instance, the conductive electrode(s) 112 can be formed on the electrode plate 100 by blanket depositing a conductive (i.e., metal) seed layer and lithographically etching the seed layer forming conductive seed regions (not shown) in areas where the conductive electrode(s) 112 are to be formed, followed by metal plating of a conductive material on the metal seed regions. The top surfaces of the conductive electrode(s) 112 are thus raised from the topmost surface of the electrode plate 100.

Figure 1B:
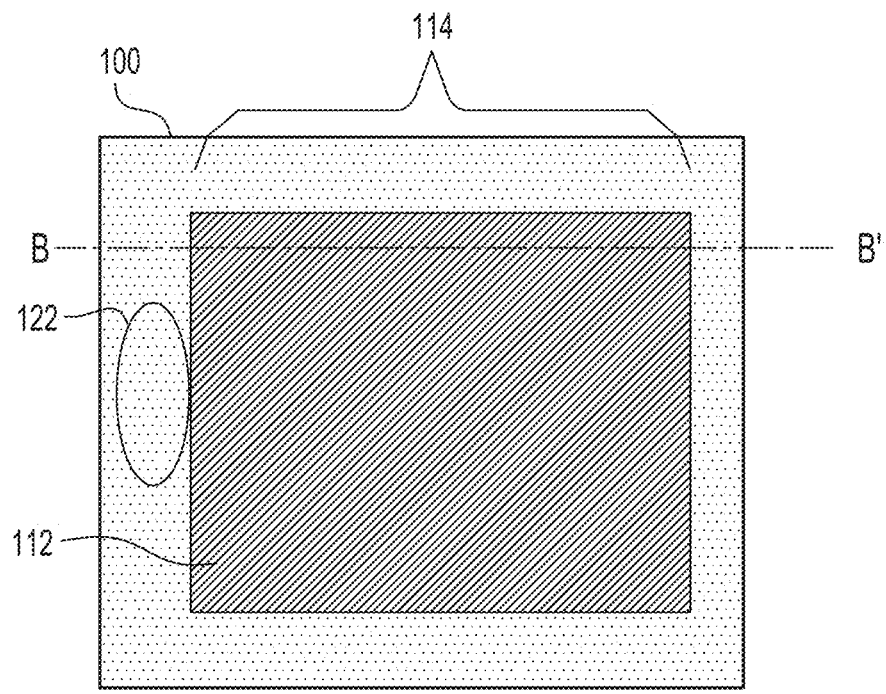
FIG. 1B is a top view of a second exemplary electrode plate that can be employed in the structures, systems and methods of the present application.
Figure 1C:
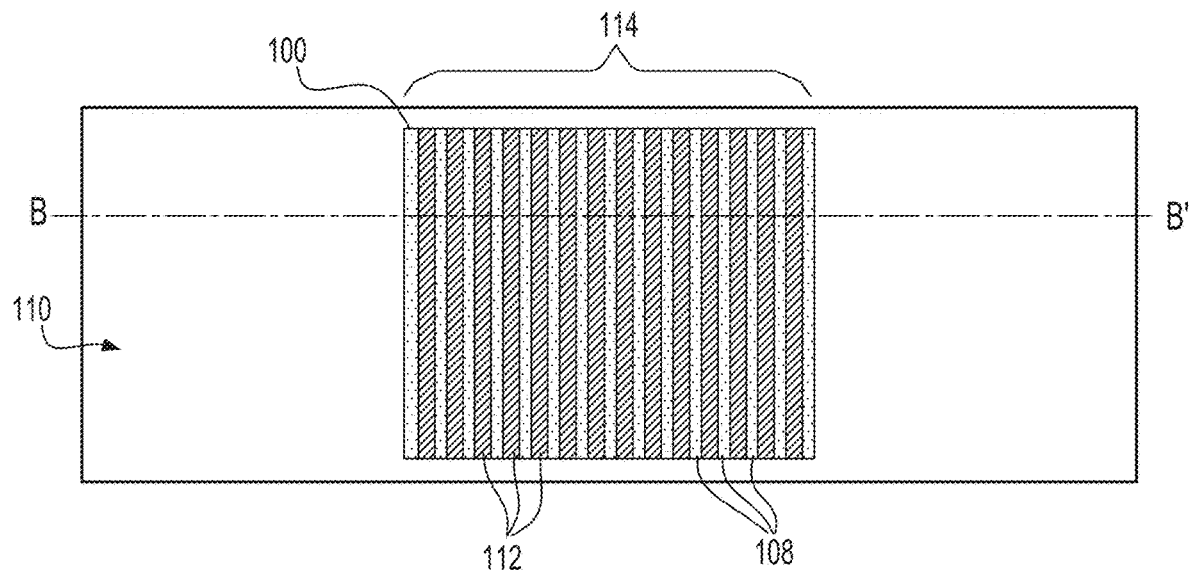
FIG. 1C is a top view of a third exemplary electrode plate that can be employed in the structures, systems and methods of the present application.
Figure 1D:
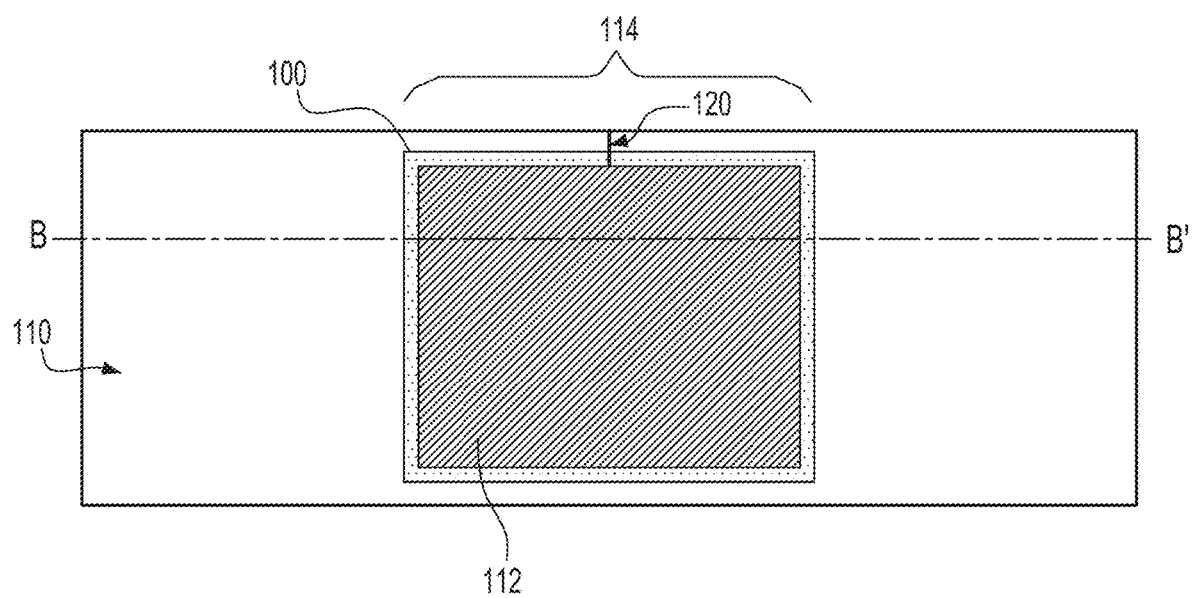
FIG. 1D is a top view of a fourth exemplary electrode plate that can be employed in the structures, systems and methods of the present application.
Figure 1E:
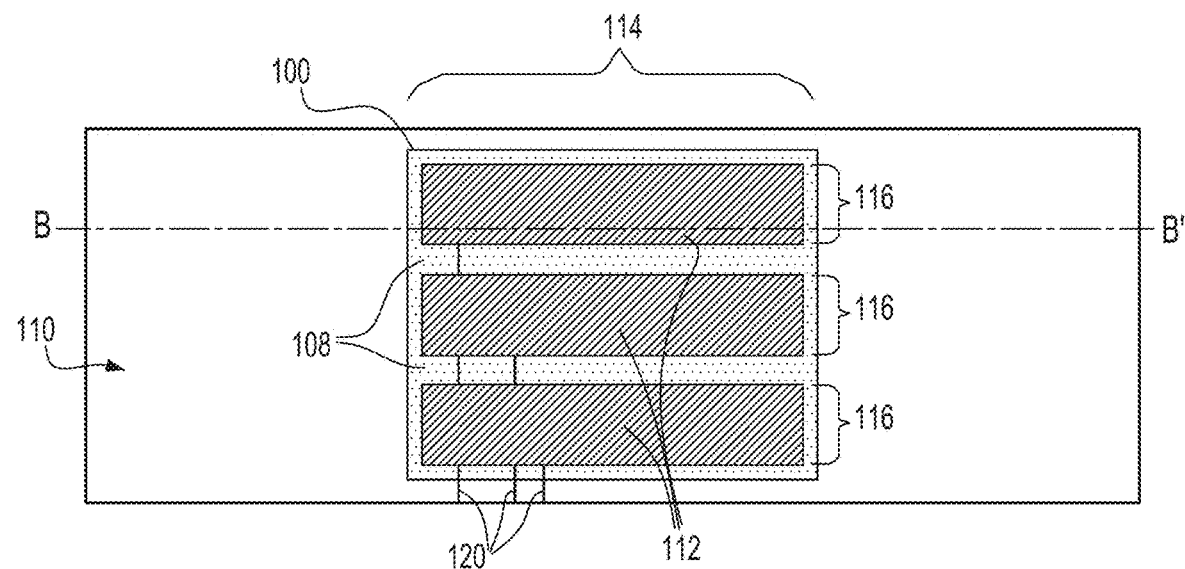
FIG. 1E is a top view of a fifth exemplary electrode plate that can be employed in the structures, systems and methods of the present application.
Figure 1F:
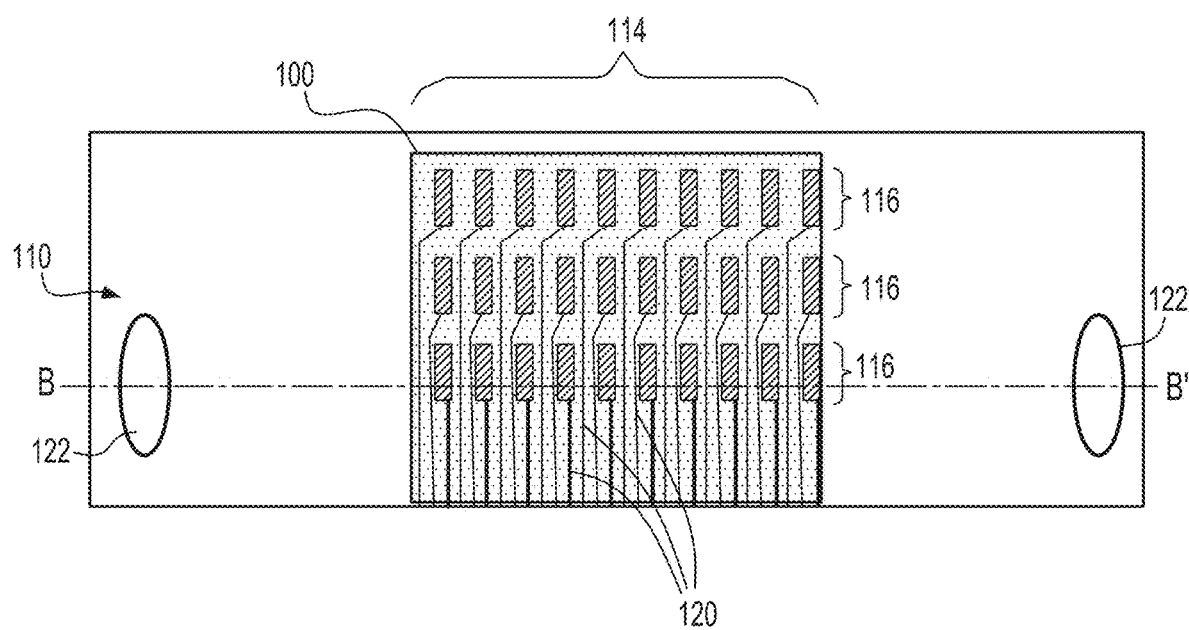
FIG. 1F is a top view of a sixth exemplary electrode plate that can be employed in the structures, systems and methods of the present application.

In FIGS. 1C, 1E and 1F, the plurality of conductive electrodes 112 are separated geographically by a lateral space 108 to form a capacitance sensing region 114. In another instance and as shown in FIG. 1B, a single (common) conductive electrode 112 is located directly on a surface of an electrode plate 100, to form a capacitance sensing region 114 of the structure.

Figure 2:
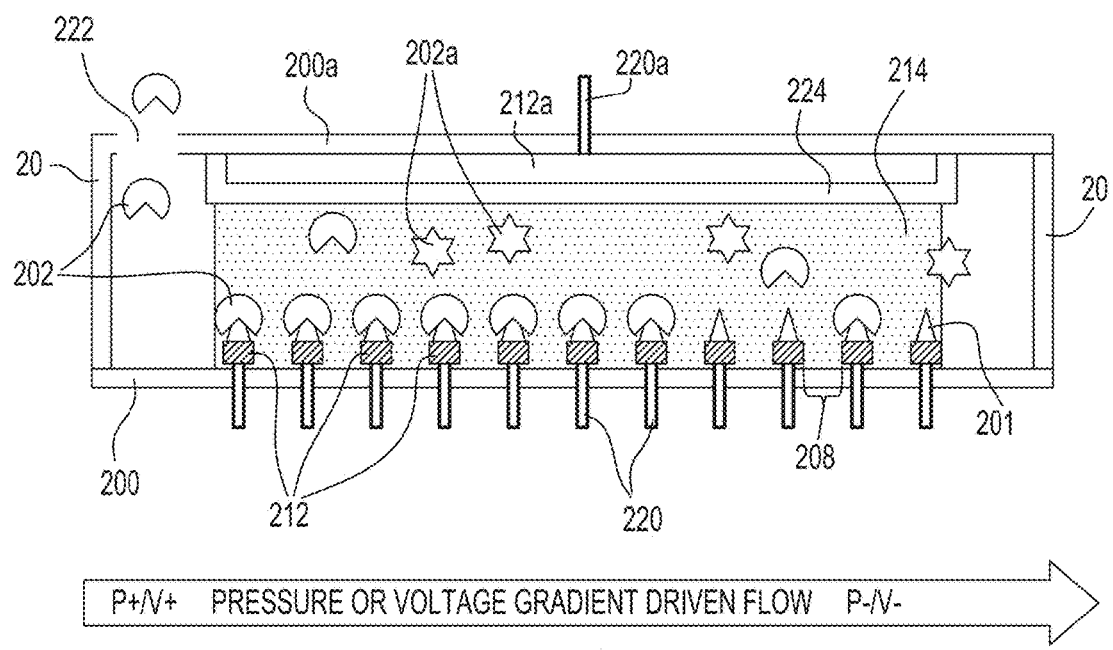
FIG. 2 is a cross-sectional view of a first exemplary micro-capacitive sensor array along line B-B'.

In instances where the conductive electrode(s) 112 are formed on a topmost surface of the electrode plate 100, after formation of the electrode(s) 112, an insulator layer (i.e., dielectric layer) 224 may be deposited on remaining exposed surfaces of the electrode plate 100 to embed the conductive electrode(s) 112 therein, as shown in FIG. 2. The insulator layer may include a dielectric material such as, for example, silicon dioxide, silicon nitride, or a low dielectric constant (low-k) material such as organosilicate glass; the term "low-k denotes a dielectric material having a dielectric constant of less than silicon dioxide. The insulator layer can be formed, for example, by CVD, PECVD or spin coating. The insulator layer is optional and can be omitted in some embodiments of the present application.

In certain embodiments, the electrode plate 100 can be formed on, or within, a substrate 110 as shown, for example, in FIGS. 1C-1I. Here, the conductive electrode(s) 112 and the electrode plate 100 can be formed as set forth above. In one embodiment and as shown in FIG. 1A, 1C, 1E-1F, an exemplary electrode plate 100 includes a plurality of conductive electrodes 112 on a first exposed surface thereof and a second surface that is directly contacted by a surface of the substrate 110.

A substrate 110 of the present disclosure may be rigid or flexible and may include an insulating layer on a semiconductor material or an electrically insulating material such as, for example, glass or a polymer. Exemplary semiconductor materials that can be employed in the present application as the top substrate 110 include, but are not limited to, Si, Ge, SiGe, SiGeC, SiC, GaSb, GaP, GaN, GaAs, InAs, InP, AlN, and all other III-V or II-VI compound semiconductors. In one embodiment, the substrate 110 is comprised of silicon. Exemplary polymers that can be employed in the present application as the substrate 110 include, but are not limited to, poly(ethylene terephthalate) (PET), poly(butylene terephthalate) (PBT), poly(enthylene naphthalate) (PEN), polycarbonate (PC), polyimides (PI), polysulfones (PSO), and poly(p-phenylene ether sulfone) (PES). In one embodiment, the substrate 110 is comprised of a polyimide. Typically, the substrate 110 is transparent and is composed of glass or a polymer. Using transparent substrates may add an additional advantage of visible viewability of changes occurring between multiple substrates. The substrate(s) 110 employed in the present application may have a thickness from a few tens of microns to a few millimeters. In another embodiment, the substrate(s) 110 employed may have a thickness from a few microns to a few millimeters. The substrate 110 can have other thicknesses that are above and/or below the ranges mentioned above.

Figure 1G:
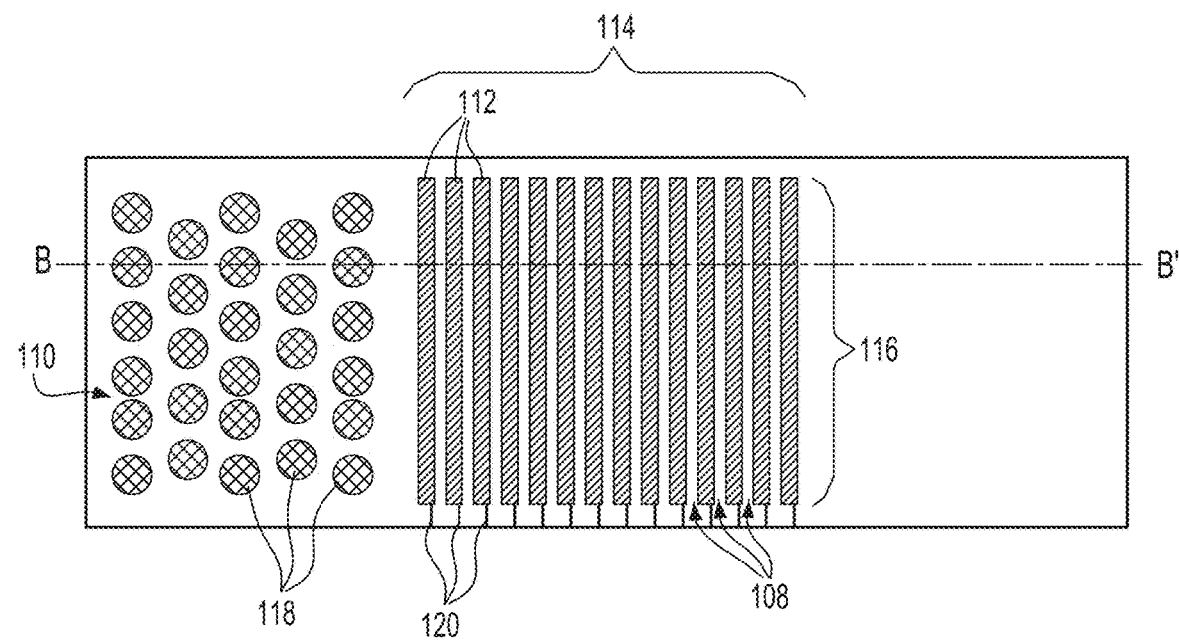
FIG. 1G is a top view of an exemplary structure that can be employed in the arrays, systems and methods of the present application.
Figure 1H:
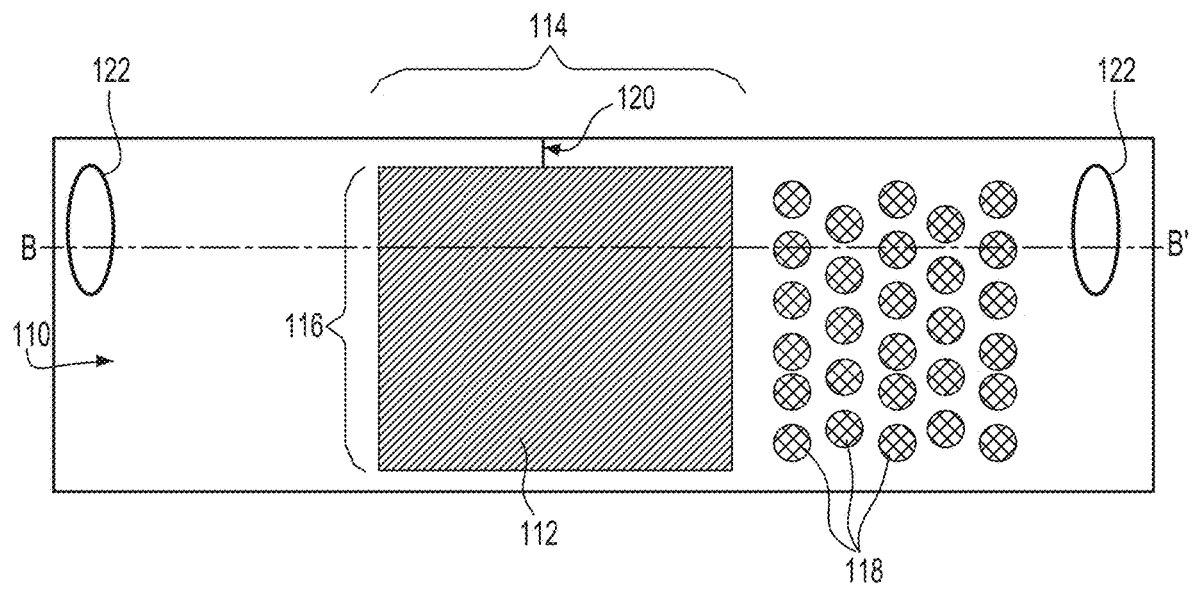
FIG. 1H is a top view of another exemplary structure that can be employed in the arrays, systems and methods of the present application.
Figure 1I:
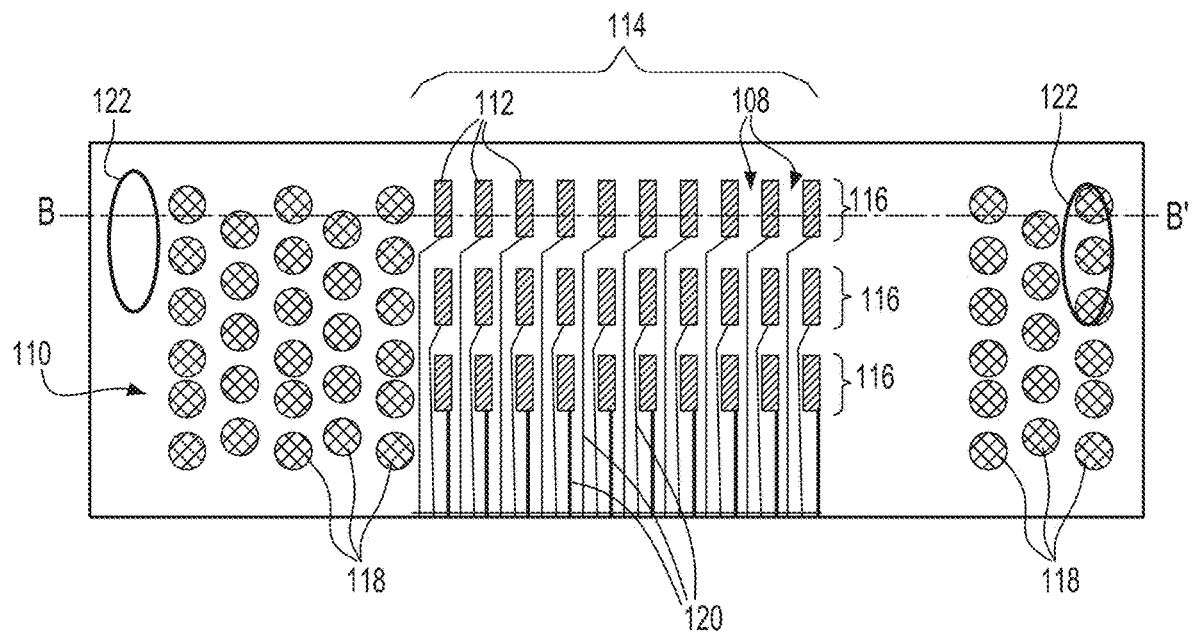
FIG. 1I is a top view of a yet another exemplary structure that can be employed in the arrays, systems and methods of the present application.

In certain embodiments, such as those shown in FIGS. 1G-1I the at least one conductive electrodes 112 are formed directly on, or are embedded within, the substrate 110. In one embodiment and as shown in FIG. 1G, an exemplary micro-capacitance sensor array includes a plurality of conductive electrodes 112 on a first exposed surface of a substrate 110. As stated above, the plurality of conductive electrodes 112 are separated geographically by a lateral space 108 to form a capacitance sensing region 114. In some embodiments and as shown in FIG. 1H, a single (common) conductive electrode 112 is located directly on or is embedded within an exposed surface of a substrate 110.

In certain embodiments, such as those shown in FIGS. 1G-1I, the at least one conductive electrodes 112 can be formed in trenches within the substrate 110. For example, the at least one conductive electrode 112 can be formed within the substrate 110 by conventional lithography, etching and deposition processes. More specifically, a photoresist layer may first be formed on the substrate 110 and exposed to light to form a desired pattern of openings therein. An anisotropic etch such as, for example, a reactive ion etch (RIE), may then be performed to form trenches in the substrate 110 using the patterned photoresist layer as an etch mask. The trenches can be filled with a conductive material such as, for example, a transparent conductive oxide, such as a tin oxide (e.g., indium tin oxide (ITO), fluorine doped oxide (FTO)), gold, silver, nickel, copper, tungsten, aluminum or alloys thereof to provide the desired number and distribution of conductive electrodes 112. The surface of the structure can be planarized using a planarization process such as, for example, chemical mechanical polishing (CMP). After planarization, the top surface(s) of the conductive electrode(s) 112 are coplanar with the top surface of the substrate 110 or electrode plate 100.

In another embodiment, the conductive electrode(s) 112 are formed on the substrate 110 by blanket depositing a conductive material followed by lithographically etching the conductive material. For example, a conductive material may be first blanket deposited directly on the substrate 110 using a conventional deposition process such as, for example, chemical vapor deposition (CVD), physical vapor deposition (PVD), plasma-enhanced vapor deposition (PECVD), or atomic layer deposition (ALD). A photoresist layer may then be formed on the conductive material, and exposed to light to form openings therein. The exposed conductive material may then be removed using RIE, through the openings, to form the conductive electrodes 112 using the patterned photoresist layer as an etch mask. Subsequently, the patterned photoresist layer may be removed, for example, by ashing. Here, the topmost surface(s) of the conductive electrodes 112 are thus located above the topmost surface of the substrate 110.

Figure 6A:
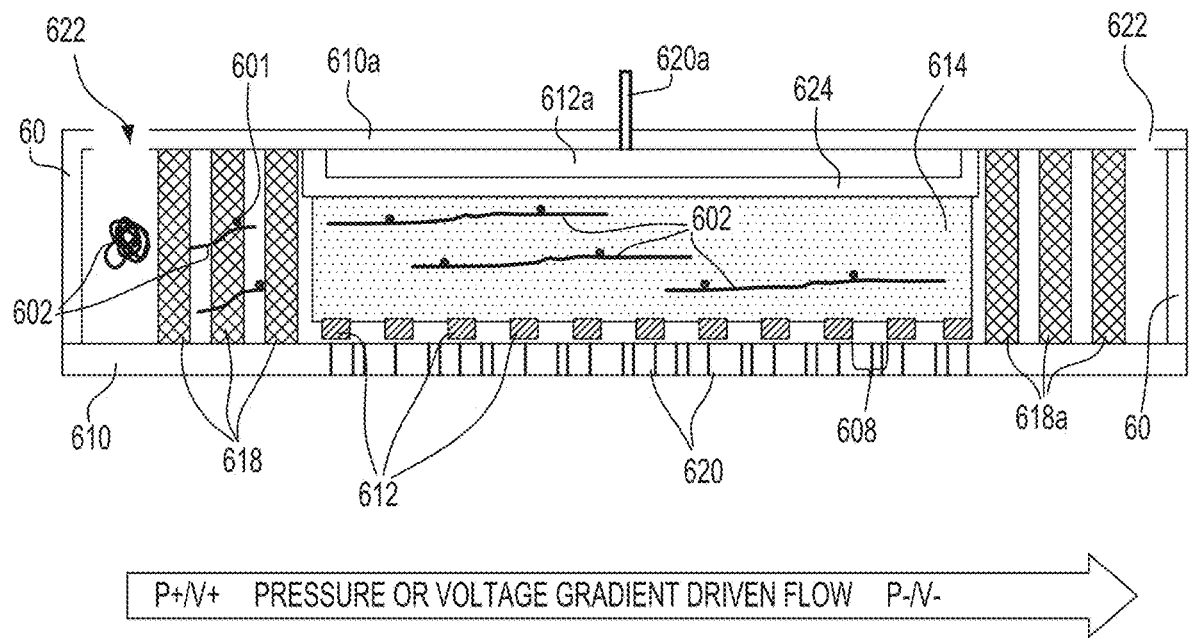
FIG. 6A is a cross-sectional view of a third exemplary micro-capacitive sensor array along line B-B'.

In yet another embodiment, the conductive electrode(s) 112 can be formed on the substrate 110 by blanket depositing a conductive (i.e., metal) seed layer and lithographically etching the seed layer form conductive seed regions (not shown) in areas where the conductive electrode(s) 112 are to be formed, followed by metal plating of a conductive material on the metal seed regions. The top surfaces of the conductive electrode(s) 112 are thus raised from the topmost surface of the substrate 110, as shown in FIG. 6A.

In instances where the conductive electrodes 112 are formed on a topmost surface of the substrate 110, after formation of the electrodes 112, an insulator layer (i.e., dielectric layer) may be deposited on remaining exposed surfaces of the substrate 110 to embed the conductive electrode(s) 112 therein, as shown in FIG. 2. The insulator layer may include a dielectric material such as, for example, silicon dioxide, silicon nitride, or a low dielectric constant (low-k) material such as organosilicate glass; the term "low-k denotes a dielectric material having a dielectric constant of less than silicon dioxide. The insulator layer can be formed, as above by CVD, PECVD or spin coating. See FIG. 6A.

In instances where the structure contains a capacitance sensing region 114 such as that shown in FIGS. 1A through 1I, the capacitance sensing region 114 comprises at least one channel, such as a nanochannel 116. The at least one channel 114 is located between overlapping portions of a first electrode plate 100 and a second electrode plate 100a, or between overlapping portions of the capacitive electrodes 112 of a first substrate 110 and a second substrate 110a. In certain embodiments, the at least one channel 114 can include one, two, three, four, five or more nanochannels 116 through/over which an analyte (e.g., a nucleic acid) can travel. In some instances, analytes can travel across the nanochannel(s) 116 in a direction that is perpendicular to the direction of a pressure gradient or voltage gradient across the structure. In some embodiments, the at least one nanochannel 116 can include a single (common) conductive electrode 112, such as is shown in FIG. 1E. In other embodiments, the at least one nanochannel 116 can include a plurality of conductive electrodes 112, as in FIG. 1G. In yet other embodiments, such as that shown in FIGS. 1F and 1I, the at least one nanochannel 116 includes more than one plurality of conductive electrodes 112, such that each plurality of conductive electrodes 112 forms a nanochannel 116.

In some instances and as illustrated in FIGS. 1B and 1H-1I, a substrate 110 or electrode plate 100 can have an opening (i.e., through hole) 122 therein through which a plurality of analytes or a solution containing an analyte can be introduced to the at least one channel 114 for sensing an analyte. For example, as shown in FIG. 1H, two openings 122 are formed at opposite ends of the at least one channel 114 for sensing an analyte with one being an analyte inlet port and the other one being a outlet port. In another embodiment, the one or more openings 122 can all serve as an analyte inlet port. The openings 122 may be formed through the substrate 110 or electrode plate 100 by any method know in the art such as, for example, laser drilling, etching or mechanical drilling.

As shown in FIGS. 1G-1I, in certain instances the structure of the present application includes at least one array of vertical pillars 118. The vertical pillars of the array of vertical pillars 118 can be formed, for example, of a dielectric material or a semiconductive material. A dielectric material such as, for example, silicon dioxide, silicon nitride, or a low dielectric constant (low-k) material such as organosilicate glass; the term "low-k denotes a dielectric material having a dielectric constant of less than silicon dioxide. A semiconductive material can be any semiconductive material, as set forth above. For example, a material may first be deposited directly on the substrate 110 using a conventional deposition process such as, for example, chemical vapor deposition (CVD), physical vapor deposition (PVD), plasma-enhanced vapor deposition (PECVD), or atomic layer deposition (ALD). A photoresist layer may then be formed on the material, and exposed to light to form openings therein. The exposed material may then be removed using RIE to form the pillars of the array of vertical pillars 118 using a patterned photoresist layer as an etch mask. Subsequently, the patterned photoresist layer may be removed, for example, by ashing. In some embodiments, the pillars of the array of pillars are randomly placed on a substrate 110. In other embodiments, the pillars of the array of pillars are spaced apart such that the space between each adjacent pillar in the array of pillars is smaller than the size of an analyte, such as DNA or RNA in solution. In the case of DNA or RNA, the space between pillars can be smaller than the analyte's radius of gyration ($R_g$) enabling the nucleic acid analyte to stretch into a linear configuration when forced to pass through the constricted space between the pillars. Here, when a gradient (e.g., pressure or voltage) is applied to the micro-capacitive sensor array of the present disclosure causing the analyte to traverse an array of vertical pillars 118, the DNA or RNA analyte will lengthen to form a linear analyte prior to traversing the at least one channel for sensing an analyte, i.e., capacitance sensing region 114. Hence, an array of vertical pillars 118 can be located on a portion of the substrate 110 adjacent to the at least one channel 114 for sensing an analyte. In certain embodiments, the micro-capacitive device of the present disclosure includes two arrays of vertical pillars 118. Here, as shown in FIG. 1I the first and second array of vertical pillars 118 are each located on the substrate 110 such that the first array of vertical pillars 118 is located on first a portion of the substrate 110 adjacent to the at least one channel 114 for sensing an analyte and the second array of vertical pillars 118 is located on another portion of the substrate 110 adjacent to the at least one channel 114 for sensing an analyte, such that each of the at least one array of vertical pillars 118 are on opposing sides of the channel 114 for sensing an analyte.

The vertical pillars 118 can be coated with a label or nanoparticle capable of binding to an analyte. The vertical pillars 118 may coated by depositing a blanket layer (not shown) containing a label on exposed surfaces of a substrate 110, the conductive electrodes 112, an electrode plate 100, the vertical pillars 118 or any combination thereof. In other embodiments, the label containing layer may be selectively deposited on one or more of a substrate 110, the conductive electrodes 112, an electrode plate 100 and the vertical pillars 118. Any label capable of binding (e.g., covalently, electrostatically, or by intercalation) to an analyte of interest can be used that produces a detectable signal, and such labels are known to those of ordinary skill in the art. Exemplary labels include, but are not limited to, quantum dots, nanoparticles, fluorescent molecules, ethidium bromide, proflavine, daunomycin, doxorubicin, 5-flurouracil, thalidomide, antibodies, oligomers or radiolabels that are provide a detectable signal. Here, when an analyte, e.g., a DNA molecule, comes in contact with a label coated vertical pillar 118 the label will bind selectively to the analyte facilitating detection of the label through the at least one channel 114 for sensing an analyte. In other embodiments, an exposed surface of the conductive electrodes 112 are coated with a solution containing a label or plurality of labels. Here, the labels are capable of binding to an analyte in a nanochannel 116 within the at least one channel 114 for sensing an analyte. In certain instances the label is an antibody specific to an analyte, such as a viral surface protein, that anchors the analyte to the nanochannel 116 or a conductive electrode 112 when contacted.

As shown, for example, in FIGS. 1E-1I, micro-capacitive sensor arrays of the present application contain conductive circuit lines 120 to which a current may be applied to form an electric field in a first direction across the at least one nanochannel 116 within the at least one channel 114 for sensing an analyte. The conductive circuit lines are capable of providing current to one electrode 112 relative to all the other electrodes, or one nanochannel 116 relative to all other nanochannels. In certain embodiments, the first electrode plate or substrate includes a plurality of first conductive electrodes having a first polarity that are spaced apart and electrically isolated from one another and said second electrode plate or substrate contains a conductive electrode of a second polarity.

Referring to FIG. 2, a side view of a first exemplary micro-capacitive sensor array of the present application is provided. In this embodiment, a first electrode plate 200 includes a plurality of conductive electrodes 212 formed on, or embedded within, the first electrode plate 200, as shown in FIG. 1A. Each of the conductive electrodes 212 of the first electrode plate are parallel and separated by spaces 208 and traverse the entire width of the channel 214 for sensing an analyte 202. In this embodiment, the exposed uppermost surface of each of the plurality of conductive electrodes 212 are coated with a plurality of labels (i.e., an antibody) 201 capable of binding to a desired analyte 202, while the labels do not bind other analytes (i.e., non-desirable) present in the sample 202*a*, as discussed above.

As used herein, the term "analyte" or "analytes" is any biomolecule that can be recognized. In some embodiments, an analyte is a polypeptide. As used herein, a "polypeptide" is a single polymer chain of amino acids bonded together by peptide bonds between the carboxyl and amino groups of adjacent amino acid residues. The term "protein" includes polypeptide. The term "protein" may also be used to describe a polypeptide, having multiple domains, such as beta sheets, linkers and alpha-helices. As such, the term "protein" is also meant to include polypeptides having quaternary structures, ternary structures and other complex macromolecules composed of at least one polypeptide. If the protein is comprised of more than one polypeptide that physically associate with one another, then the term "protein" as used herein refers to the multiple polypeptides that are physically coupled and function together as the discrete unit.

In embodiments of the present methods, an analyte is any polypeptide that includes an epitope or amino acid sequence of interest. Such polypeptide can be isolated from cells, synthetically produced, or recombinantly produced using means known by those of ordinary skill in the art. In some embodiments, an analyte is any polypeptide that includes an epitope or amino acid sequence of interest. In certain embodiments, polypeptide (protein) analytes can be isolated from cells or viruses, synthetically produced, or recombinantly produced. In one embodiment, an analyte is a protein or a fragment thereof that has been produced by a cell or virus. In certain embodiments, the analyte is a protein that is present on the outermost surface of the cellular membrane or viral capsid. In one embodiment, the protein present on the outermost surface of the cellular membrane or viral capsid has an antigen or epitope that is accessible to a label (e.g., antibody, dye). In yet other embodiments, an analyte is a protein or a fragment thereof that has been secreted by a cell.

In certain exemplary embodiments, an analyte is hemagglutinin present on a surface of an influenza virus, a derivative, analog or homolog thereof. In other exemplary embodiments, an analyte is a cell surface protein known by those of ordinary skill in the art. In other embodiments, the analyte is a nucleic acid. The nucleic acid analyte can be a deoxyribonucleic acid (DNA), e.g., genomic DNA or isolating coding DNA. In other embodiments, the nucleic acid analyte can be a ribonucleic acid (RNA), such as messenger RNA, ribosomal RNA molecule. The nucleic acid analyte can be single stranded or double stranded.

In certain embodiments, the analyte 202 of interest can be affixed (bound) to a detectable label. The term "label" or "detectable label" as used herein means a molecule, such as a dye, nanoparticle, oligonucleotide, or an antibody that is capable of binding to an analyte of interest when contacted by the analyte. A label may be directly detectable (e.g., fluorescent moieties, electrochemical labels, electrochemical luminescence labels, metal chelates, colloidal metal particles, quantum dots), as well as a molecule or molecules that may be indirectly detected by production of a detectable reaction product (e.g., enzymes such as horseradish peroxidase, alkaline phosphatase and the like), a molecule or molecules that can be detected by recognition of a molecule that specifically binds to the detection antibody such as, a labeled antibody that binds to the detection antibody, biotin, digoxigenin, maltose, oligohistidine, 2,4-dintrobenzene, phenylarsenate, a nucleic acid (e.g., ssDNA, dsDNA) or the like).

Labels for use in the present application can be provided on the surface of a vertical pillar 118 or a conductive electrode 112 or a label can be provided to a sample prior to introduction to a micro-capacitive sensor array of the present application. In certain embodiments, the label is affixed to a structure such as a vertical pillar 118 or a conductive electrode 112 such that a binding portion (e.g., antigen-binding portion of an antibody) of the label is positioned such that the binding portion can be contacted by the portion of the analyte to which it binds (e.g., antigen) when presented thereto. In other instances, a structure such as a vertical pillar 118 or a conductive electrode 112 can be coated with a label, which when contacted with an analyte removes the label from the structure.

A "sample" or a portion thereof is provided to a micro-capacitive sensor array of the present application. The sample contains at least one analyte of interest, such as a protein or nucleic acid. Regardless of the number of analytes or analytes of interest, the sample can be readily applied to a micro-capacitive sensor array of the present application. In certain embodiments, a sample may be obtained from a subject, or may be obtained from other materials. The term "subject" as used herein refers to a human or non-human organism. Thus, the methods described herein are applicable in both human and veterinary fields. Further, while a subject is preferably a living organism, the methods described herein may be used in post-mortem analysis as well. Subjects that are humans can be "patients," which as used herein refers to living humans that are receiving or may receive medical care for a disease or condition.

In some instances, the sample is created for the purpose of determining the presence of certain analytes therein. For example, a sample may be obtained from cell culture, a fluid or tissue known to include, or not include, the analyte(s) of interest. In other instances, the sample is created by adding synthetic or recombinantly produced peptides to a solution that is easily stored and dispensed. In specific embodiments, samples for use in the present methods are body fluid samples obtained from a subject, such as a patient. In some embodiments, samples of the present disclosure include blood, tears serum, plasma, cerebrospinal fluid, urine, saliva, sputum, and pleural effusions. One of skill in the art would realize that certain samples would be more readily analyzed following processing, e.g., fractionation or purification. For example, fractionation of whole blood obtained from a subject into serum and/or plasma components. Hence, a sample can be used as is, or can be treated to result in a final sample for detection of analytes. For example, a sample can be liquefied, concentrated, dried, diluted, lyophilized, extracted, fractionated, subjected to chromatography, purified, acidified, reduced, degraded, subjected to enzymatic treatment, or otherwise treated in ways known to those having ordinary skill in the art in order to release an analyte of interest. If desired, a sample can be a combination (pool) of samples, e.g., from an individual or from a manufacturing process.

A sample can be in a variety of physical states, such as liquid, solid, emulsion, or gel. Samples can be treated with customary care to preserve analyte integrity. Treatment can include the use of appropriate buffers and/or inhibitors, such as inhibitors of certain biological enzymes. One having ordinary skill in the art will be able to determine the appropriate conditions given the analytes of interest and the nature of the sample.

For example, the sample may be liquid and the amount of a liquid sample provided to a micro-capacitive sensor array of the present application can be from 1-100 mL, 1-50 mL, 1-40 mL, 1-30 mL, 1-20 mL, 1-10 mL, 1-5 mL, 1-4 mL, 1-3 mL, 1-2 mL or less than 2 mL of sample. In some embodiments, the amount of liquid sample is from 1-100 µL, 1-50 µL, 1-40 µL, 1-30 µL, 1-20 µL, 1-10 µL, 1-5 µL or less of sample.

The first exemplary micro-capacitive sensor array of the present application set forth in FIG. 2 also includes a second electrode plate 200a that is composed of single common conductive electrode 212a formed on, or embedded within, the second electrode plate 200a, as shown in FIG. 1B. In the exemplary embodiment provided in FIG. 2, an optional insulator layer 224 is formed on the entire exposed surface of the common conductive electrode 212a. In the present embodiment, the first electrode plate 200 and the second electrode plate 200a are arranged in an overlapping and parallel configuration forming the channel for sensing an analyte 214 between the first and second electrode plates. In the depicted embodiment of FIG. 2, the first electrode plate 200 and the second electrode plate 200a are completely overlapping. However, in some embodiments, the first electrode plate 200 and the second electrode plate 200a can be partially overlapping to form a channel 214 for sensing an analyte 202 between overlapping portions of the first and second electrode plates. The second electrode plate can include opening 222 in a portion thereof that is adjacent to the channel 214 for sensing an analyte 202. Each of the conductive electrodes 212/212a of the first electrode plate 200 and the second electrode plate are 200a are connected to a conductive circuit line 220/220a, through which a current can be applied to form an electric field within the channel 214 for sensing an analyte 202. In certain instances, the first electrode plate includes a plurality of first conductive electrodes having a first polarity that are spaced apart and electrically isolated from one another and said second electrode plate contains a single conductive electrode of a second polarity.

The first electrode plate 200 is spaced away from the second electrode plate 200a by a plurality of spacers 20. The spacers 20 set the distance between the first electrode plate 200 and the second electrode plate 200a. The height of the spacers 20 can be adjusted to obtain the best measurement resolution. The height of the spacers 20 can be from 1 nm to 1 cm. The spacers 20 can be disposed around the periphery of one of the first electrode plate 200 and the second electrode plate 200a. It should be noted that although 2 spacers 10 are illustrated in FIG. 2, additional spacers 20 may also be used for increased mounting stability of the first electrode plate 200 and the second electrode plate 200a. The spacers 20 can be deposited on one of the electrode plates 200/200a before the array is constructed.

Spacers 20 are typically made from a rigid material having a high tensile strength. In one embodiment, the spacers 20 may be made of a ceramic. Exemplary ceramics include, but are not limited to, $TiO_2$, $Ta_2O_5$, $BaTiO_3$, $SrTiO_3$, $PbZrTiO_3$, $LiNbO_3$, $PbMgTiO_3$, and $PbMgNbO_3$. In another embodiment, the spacers 10 may be made of a polymer. Exemplary polymers include, but are not limited to, epoxies, polyimides, polyurethanes, parylene, polysulfones, polysulfides, benzylcyclobutenes (BCBs), nylons, polyvinylidene fluoride (PVDF), and phenolic. In yet another embodiment, the spacers 20 may be made of insulators commonly used in microelectronic fabrication such as, for example, various oxides or nitrides, or are made of conductors that are insulated coated such as, for example copper or aluminum passivated by oxide or nitride layers.

The spacers 20 can also be in the form of a ring (herein referred to as gasket 20a, not shown). The gasket 20a is formed along the periphery of an electrode plate 200/200a, separating the first electrode plate 200 and the second electrode plate 200a and enclosing at least one channel 214 for sensing an analyte 202.

The gasket 20a can be formed by methods known in the art. In one embodiment, the gasket 20a may be formed from mirror twins of a solder material with a first gasket (not shown) formed on one of the electrode plates 200/200a and a second gasket (not shown) formed on the other the electrode plate 200/200a. Exemplary solder materials that can be employed in the present application include, but are not limited to, tin/copper, tin/silver (which high concentration of silver), tin/gold, SAC (tin with small percentages of aluminum and copper), and nickel with SAC. During the assembly process, once the first gasket and the second gasket are mated, the solder material is reflowed to provide the gasket 20a. In another embodiment, the gasket 20a may be formed via mechanical interlock. In yet another embodiment, the gasket 20a may be simply provided by forming an epoxy gasket on one of the electrode plates 200/200a.

The gasket 20a may also be used to assure sample containment within the at least one channel for sensing an analyte 214, after a sample has been provided to the micro-capacitive sensor array. In some embodiments and as shown, the second electrode plate 200a may also include one or more openings 222 through which a sample containing an analyte of interest 202 can be introduced into the channel 214. For example, an opening 222 can be formed at opposite ends of an electrode plate 200/200a adjacent to the channel 214 with one being an inlet port and the other one being an outlet port. In another embodiment, the one or more openings 222 can all serve as inlet ports for providing a sample.

Figure 3:
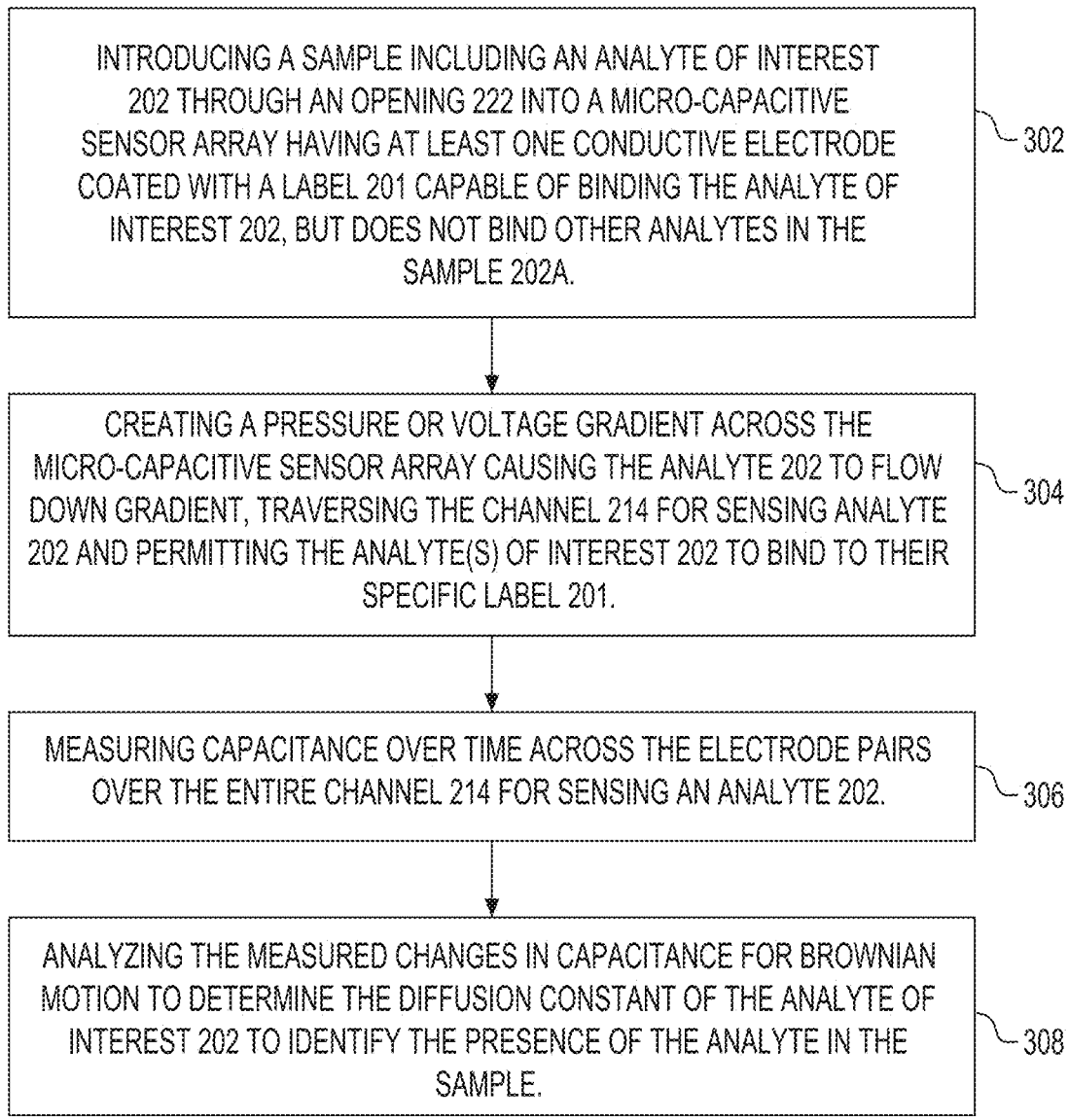
FIG. 3 is a flowchart illustrating a method of using the micro-capacitive sensor array of the present application to detect the presence of an analyte in a sample.

FIG. 3 is a flowchart illustrating a sensing process using the exemplary micro-capacitive sensor array illustrated in FIG. 2 of the present application to determine the presence of an analyte of interest 202 in a sample. In step 302, a sample including an analyte of interest 202 is introduced through an opening 222 into a micro-capacitive sensor array having at least one conductive electrode coated with a label 201 capable of binding the analyte of interest 202, which does not bind other analytes 202a in the sample. The sample including an analyte of interest 202 can be introduced by flowing the solution into one opening 222 and flow out from another opening 222 (not shown). Here, the sample including an analyte of interest 202 can be introduced into micro-capacitive sensor array after the first electrode plate 200a and second electrode plate 200 are assembled to form an exemplary micro-capacitive sensor array of the present disclosure and a pressure or electrophoretic gradient is created causing the sample to flow down gradient, traversing the channel for sensing analyte 214 and permitting the analyte(s) of interest 202 to bind to their specific label 201, as shown in step 304. In step 306, capacitance across the conductive electrodes 212 pairs over the entire capacitive sensor array is measured. The capacitance can be measured between neighboring capacitive electrodes 212 in the same electrode plate or between intersecting electrodes on the first and second electrode plates 212/212a. In step 306, as the sample flows through the channel 214, the capacitance change across the channel 214 is monitored. By recording the capacitance of electrode pairs over time, a 2D map of the capacitance of the entire micro-capacitive sensor array can be generated. As stated in step 308, any capacitance change between electrode pairs can be analyzed for Brownian motion to determine the diffusion constant of the analyte of interest 202 to identify the presence of the analyte in the sample.

Figure 4:
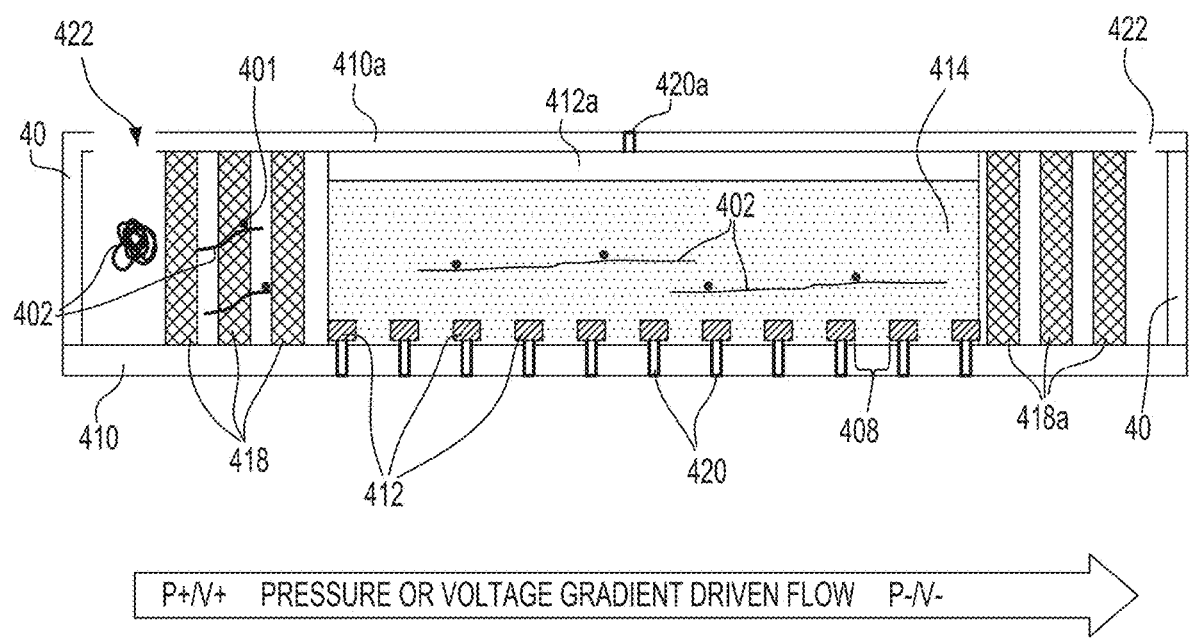
FIG. 4 is a cross-sectional view of a second exemplary micro-capacitive sensor array along line B-B'.

In a second embodiment of the present disclosure, and as shown in second the exemplary micro-capacitive sensor array of FIG. 4, a first substrate 410 includes a plurality of conductive electrodes 412 formed on, or embedded within, the first substrate 410, as shown in FIG. 1G. Each of the conductive electrodes 412 of the first substrate 410 are parallel and separated by spaces 408 and traverse the entire width of the channel 414 for sensing an analyte. In this embodiment, the desired analyte 402 is a nucleic acid, such as DNA or RNA. Here, the analyte is bound by a label 401, such as short oligonucleotide comprising an interchelating agent, a nanoparticle, or a quantum dot, as discussed above.

The second exemplary micro-capacitive sensor array of the present application set forth in FIG. 4 also includes a second substrate 410a that includes a single (common) conductive electrode 412a formed on, or embedded within, the second substrate 410a, as shown in FIG. 1H. In the exemplary embodiment provided in FIG. 4, an optional insulator layer 224 is not shown. However, in alternative configurations of the exemplary micro-capacitive sensor array an insulator layer 224 can be formed on the entire exposed surface of the conductive electrode(s) 412/412a or a portion thereof.

In the present embodiment, the first substrate 410 and the second substrate 410a are arranged in an overlapping and parallel configuration forming the channel for sensing an analyte 414 between the first and second substrates 410/410a. In the depicted embodiment of FIG. 4, the first substrate 410 and the second substrate 410a are completely overlapping. However, in some embodiments, the first substrate 410 and the second substrate 410a can be partially overlapping to form a channel 414*for* sensing an analyte between overlapping portions of the first and second substrates. The second substrate 410a can include opening 422 in a portion thereof that is adjacent to the channel 414 for sensing an analyte. In this embodiment a surface of at least one array of vertical pillars 418 are located on the surface of the first substrate 410 and the surface of the second substrate 410a such that a first array of vertical pillars 418 is located on first a portion of the substrates 410/410a adjacent to at least one channel 414 for sensing an analyte and the second array of vertical pillars 418a is located on another portion of the first substrate 410 and second substrate 410a adjacent to the at least one channel 414, such that each of the at least one array of vertical pillars 418/418a are on opposing sides of the channel 414 for sensing an analyte. Here, when a gradient (e.g., pressure or voltage) is applied to the micro-capacitive sensor array of the present disclosure causing the DNA analyte to traverse an array of vertical pillars 418, the analyte will stretch to form a linear nucleic acid analyte prior to traversing the at least one channel 414 for sensing an analyte. The linear nucleic acid analyte 402 can be further elongated based on the depth and width of the channel 414. In fact, DNA analytes can be elongated (stretched) to within 90% of its fully elongated length in a channel having a depth and width of 50 nm or less. Therefore, the dimensions of the at least one channel 414 for sensing an analyte can be between 50 nm and 5 nm wide and between 50 nm and 5 nm deep, between 40 nm and 5 nm wide and between 40 nm and 5 nm deep, between 30 nm and 5 nm wide and between 30 nm and 5 nm deep, between 20 nm and 5 nm wide and between 20 nm and 5 nm deep, or between 10 nm and 5 nm wide and between 10 nm and 5 nm deep. In certain instances the at least one channel 414 for sensing an analyte can be less than 50 nm wide, less than 40 nm wide, less than 30 nm wide, less than 20 nm wide or less than 10 nm wide and less than 50 nm deep, less than 40 nm deep, less than 30 nm deep, less than 20 nm deep or less than 10 nm deep.

Each of the conductive electrodes 412/412a of the first substrate 410 and the second substrate 410a are connected to a conductive circuit line 420/420a, through which a current can be applied to form an electric field within the channel 414 for sensing an analyte.

The first substrate 410 is spaced away from the second substrate 410a by a plurality of spacers 40. The spacers 40 set the distance between the first substrate 410 and the second substrate 410a. The height of the spacers 40 can be adjusted to obtain the best measurement resolution. The height of the spacers 40 can be manipulated to form the desired channel depth, as set forth above.

Figure 5:
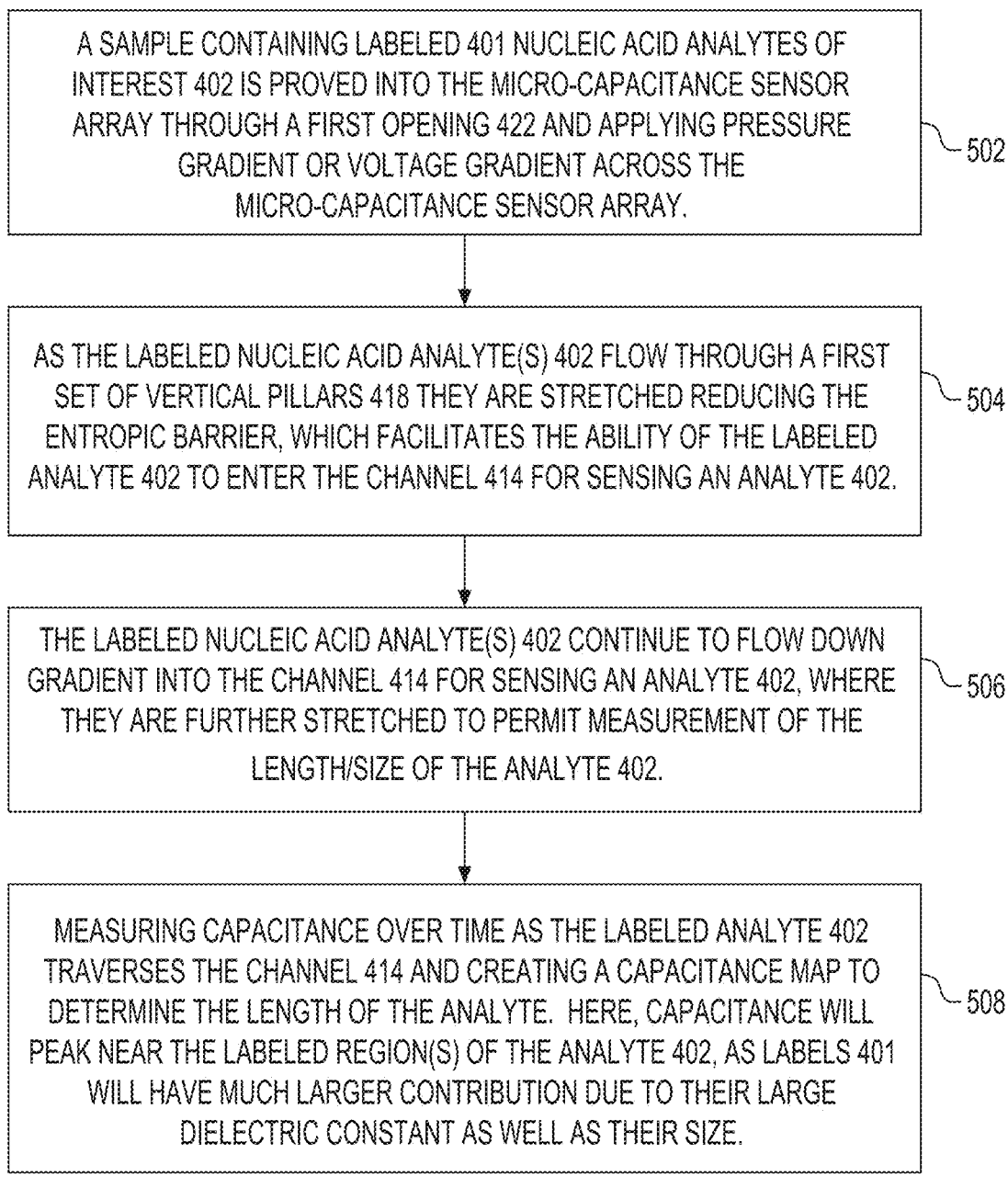
FIG. 5 is a flowchart illustrating a method of using the micro-capacitive sensor array of the present application to detect the length or presence of an analyte in a sample.

FIG. 5 is a flowchart illustrating a sensing process using the exemplary micro-capacitive sensor array illustrated in FIG. 4 of the present application to determine the length of an analyte of interest 402 in a sample. In step 502, a sample including an analyte of interest 402 is introduced through an opening 422 into a micro-capacitive sensor array having at least one array of vertical pillars adjacent to the channel 414 for sensing an analyte 402. The analyte of interest is contacted with a label 401 specific to the analyte of interest prior to flowing through the opening 422. The sample including a labeled analyte of interest 402 can be introduced by flowing the solution into one opening 422 and flow out from another opening 422 on the opposite side of the channel. Here, as shown in step 504 the sample including an analyte of interest 402 can be introduced into micro-capacitive sensor array after the first substrate 410 and second substrate 410a are assembled to form an exemplary micro-capacitive sensor array of the present disclosure and a pressure or electrophoretic gradient is created causing the sample to flow down gradient, traversing the first array of vertical pillars 418 to pre-stretch the nucleic acid analyte 402 prior to entering the channel 414 for sensing analyte 402, which further facilitates stretching of the nucleic acid analyte 402 prior to conducting a series of capacitance measurements with the channel 414 over time, as shown in step 506. In step 508, capacitance across the conductive electrodes 412 pairs over the entire capacitive sensor array is measured. The capacitance can be measured between neighboring capacitive electrodes 412 in the same electrode plate or between intersecting electrodes on the first and second substrates 410/410a. By recording the capacitance of electrode pairs over time, a 2D map of the capacitance of the entire micro-capacitive sensor array can be generated. As stated in step 508, capacitance will peak near the labeled region(s) of the analyte as labels 401 will have much larger contribution due to their large dielectric constant as well as their size.

Figure 6B:
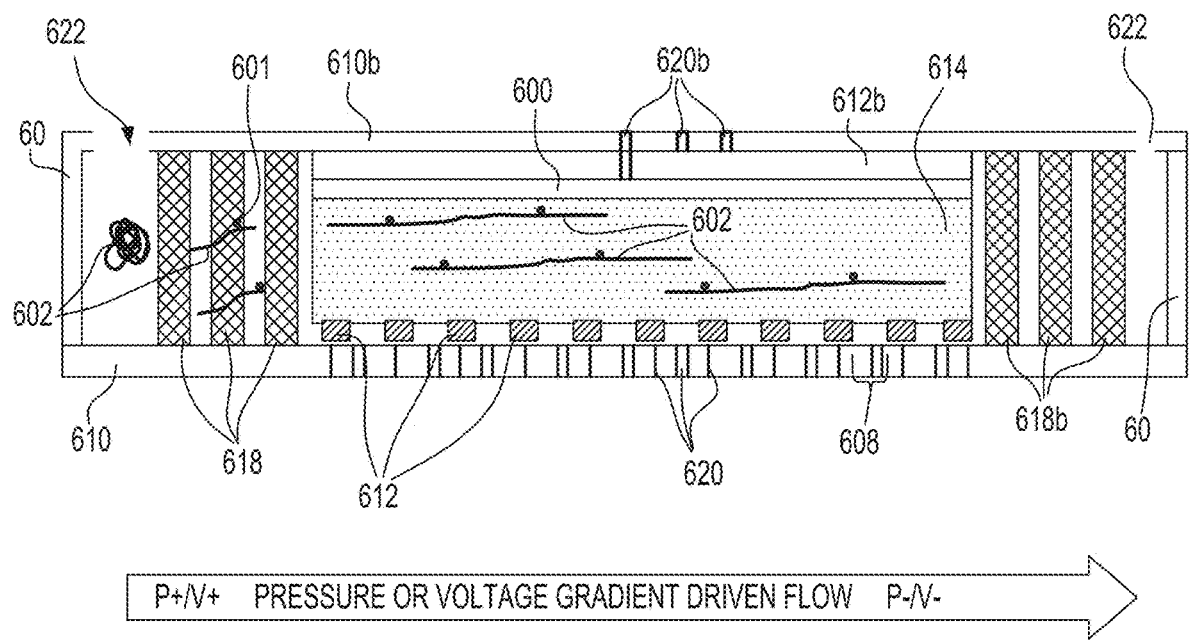
FIG. 6B is a cross-sectional view of a fourth exemplary micro-capacitive sensor array along line B-B'.
Figure 6C:
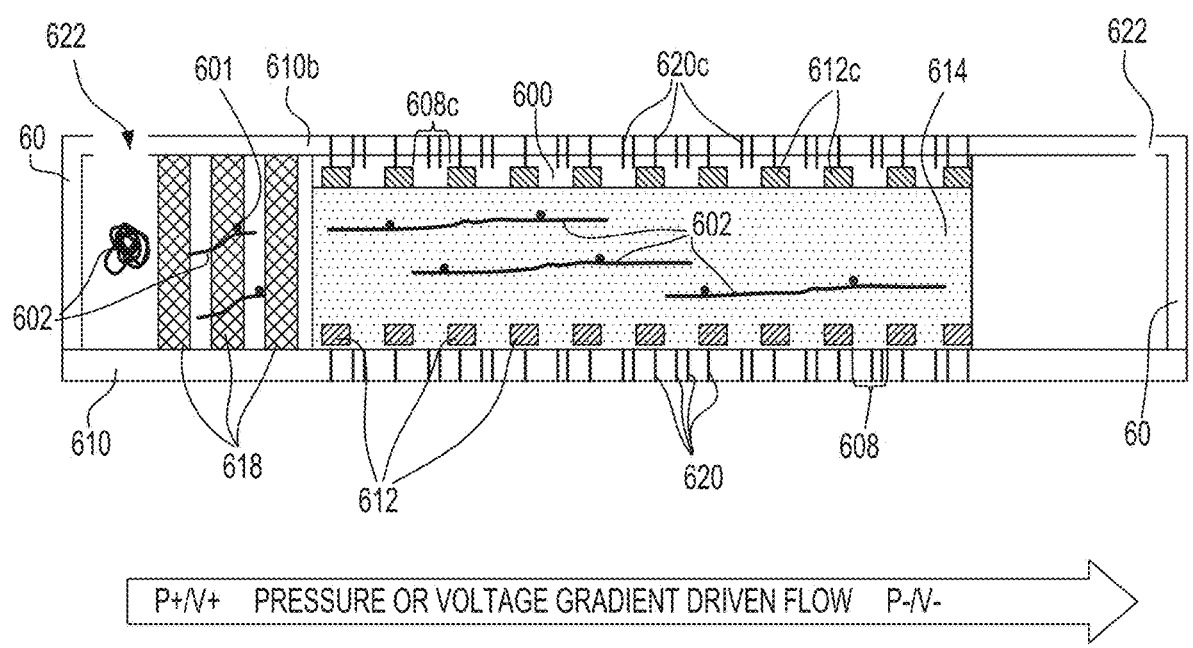
FIG. 6C is a cross-sectional view of a fifth exemplary micro-capacitive sensor array along line B-B'.

In a third embodiment of the present disclosure, and as shown in third the exemplary micro-capacitive sensor array of FIGS. 6A-C, a first substrate 610 includes a plurality of conductive electrodes 612 formed on, or embedded within, the first substrate 610, such as that shown in FIG. 1I. Each of the conductive electrodes 612 of the first substrate 610 are parallel and separated by spaces 608, which traverse the entire width of at least one nanochannel 616, such that all of the pluralities of conductive electrodes form a linear array of nanochannels across the at least one channel 614 for sensing an analyte 602, as shown in FIG. 1I. As shown, for example, in FIGS. 1I and 1F the linear array of nanochannels are located entirely within the channel 614 for sensing an analyte 602. In this embodiment, at least one array of vertical pillars 618 are located on the surface of the first substrate 610, such that a first array of vertical pillars 618 are formed on first a portion of the first substrate 610 and the second substrate 610a, 610b, 610c adjacent to the at least one channel 614 for sensing an analyte 602.

In this embodiment, the desired analyte 602 can be a nucleic acid, such as DNA or RNA. Here, the analyte is bound by a label 601, such as a short oligonucleotide comprising an interchelating agent, a nanoparticle, or a quantum dot, as discussed above. The label 601 used to bind the desired analyte can also be a fluorescent dye.

The third exemplary micro-capacitive sensor array of the present application set forth in FIGS. 6A-C also includes a second substrate 610a that includes a conductive electrode 612a formed on, or embedded within, the second substrate 610a, 610b, 610c, as shown in FIG. 1D, 1E, 1H or 1I.

In the present embodiment, the first substrate 610 and the second substrate 610a, 610b, 610c are arranged in an overlapping and parallel configuration for form the channel for sensing an analyte 614 between the first substrate 610 and second substrate 610a, 610b, 610c. In the depicted embodiment of FIGS. 6A-6C, the first substrate 610 and the second substrate 610a, 610b, 610c are completely overlapping. However, in alternative configurations of this embodiment, the first substrate 610 and the second substrate 610a, 610b, 610c can be partially overlapping to form a channel 614 for sensing an analyte 602 between overlapping portions of the first and second substrates. The second substrate 610a, 610b, 610c can include opening 622 in a portion thereof that is adjacent to the channel 614 for sensing an analyte 602.

In the exemplary embodiment provided in FIG. 6A, the second substrate 610a includes a single (common) electrode 612a formed on a surface of the second substrate 610a, such as that shown in FIGS. 1A and 1D. The configuration depicted in FIG. 6A also includes an optional insulator layer 624 formed on the entire exposed surface of the conductive electrode 612a, at least one opening 622 in a portion of the second substrate 610a adjacent to the channel 614 and an array of vertical pillars 618a, as set forth above. See, for example, FIG. 1H.

In the exemplary embodiment provided in FIG. 6B, the second substrate 610b includes a plurality of common electrodes 612b formed on a surface of an electrode plate 600, which is formed on the second substrate 610b, such as that shown in FIG. 1E. The configuration depicted in FIG. 6B also includes at least two openings 622 in a first portion of the second substrate 610b adjacent to the channel 614 and a second portion of the second substrate 610b that are on opposing sides of the at least one channel 614 for sensing an analyte. The instant configuration also includes at least two arrays of vertical pillars 618/618b formed adjacent to at least one channel for sensing an analyte such that each of the at least one array of vertical pillars 618/618b, as set forth above.

In the exemplary embodiment provided in FIG. 6C, the second substrate 610c includes a plurality conductive electrodes 612c formed on, or embedded within, an electrode plate 600, which is formed on the second substrate 610c, such as that shown in FIG. 1F. Each of the conductive electrodes 612c of the second substrate 610c are parallel and separated by spaces 608c, which traverse the entire width of at least one nanochannel 616c, such that all of the pluralities of conductive electrodes form a linear array of nanochannels across the at least one channel 614 for sensing an analyte 602, as shown in FIG. 1F. In this embodiment, one array of vertical pillars 618 are located on the surface of the second substrate 610c adjacent to the at least one channel 614 for sensing an analyte 602. The configuration depicted in FIG. 6C also includes at least two openings 622 in a first portion of the second substrate 610c adjacent to the channel 614 and a second portion of the second substrate 610c that are on opposing sides of the at least one channel 614 for sensing an analyte 602.

Here, the micro-capacitive sensing array of the present embodiment includes a first array of vertical pillars 618 located on first a portion of the first substrate 610 and the second substrate 610a, 610b, 610c adjacent to the at least one channel 614 for sensing an analyte 602. In alternative configurations of the micro-capacitive sensing array of the present embodiment a second array of vertical pillars 618a, 618b can be formed a second portion of the first substrate 610 and the second substrate 610a, 610b, 610c adjacent to the at least one channel 614 for sensing an analyte 602, such that each of the at least one array of vertical pillars 618, 610a, 610b, 610c are on opposing sides of the at least one channel 614 for sensing an analyte 602.

As in the second embodiment, when a gradient (e.g., pressure or voltage) is applied to the micro-capacitive sensor array of the present disclosure causing the nucleic acid analyte 602 to traverse the array of vertical pillars 618, the analyte will stretch to form a linear nucleic acid analyte prior to entering a nanochannel 616 and flowing across at least one channel 614 for sensing an analyte 602. The linear nucleic acid analyte 602 can be further elongated based on the depth and width of the channel 614. Here, DNA analytes 602 can be elongated to within 90% of their fully elongated length in a nanochannel having a depth and width of 50 nm or less. Therefore, the dimensions of a nanochannel 616 within the at least one channel 614 for sensing an analyte 602 can be between 50 nm and 5 nm wide and between 50 nm and 5 nm deep, between 40 nm and 5 nm wide and between 40 nm and 5 nm deep, between 30 nm and 5 nm wide and between 30 nm and 5 nm deep, between 20 nm and 5 nm wide and between 20 nm and 5 nm deep, or between 10 nm and 5 nm wide and between 10 nm and 5 nm deep. The dimensions of a nanochannel 616 within the at least one channel 614 for sensing an analyte 602 can be less than 50 nm wide, less than 40 nm wide, less than 30 nm wide, less than 20 nm wide or less than 10 nm wide and less than 50 nm deep, less than 40 nm deep, less than 30 nm deep, less than 20 nm deep or less than 10 nm deep.

In each of the configurations depicted in FIGS. 6A-6C, each of the conductive electrodes 612 of the first substrate 610 and the conductive electrode(s) 612a, 612b, 612c of the second substrate 610a, 610b, 610c are connected to a conductive circuit line 620, 620a, 620b, 620c through which a current can be applied to form an electric field within each nanochannel 616 within the channel 614 for sensing an analyte 602. This configuration of conductive electrodes 612, 612a, 612b, 612c connected by conductive circuit lines 620, 620a, 620b, 620c and nanochannels 616 facilitates the detection and monitoring of individual analytes 602, such as a nucleic acid molecule (DNA or RNA), passing through each nanochannel 616 by detecting a time sequence of capacitance measurements in each conductive electrode 612, 612a, 612b, 612c within each nanochannel 616.

As in the first two embodiments above, the first substrate 610 is spaced away from the second substrate 610a, 610b, 610c by a plurality of spacers 60. The spacers 60 set the distance between the first substrate 610 and the second substrate 610a, 610b, 610c. The height of the spacers 60 can be adjusted to obtain the best measurement resolution. The height of the spacers 60 can be manipulated to form the desired nanochannel depth, as set forth above.

Figure 7:
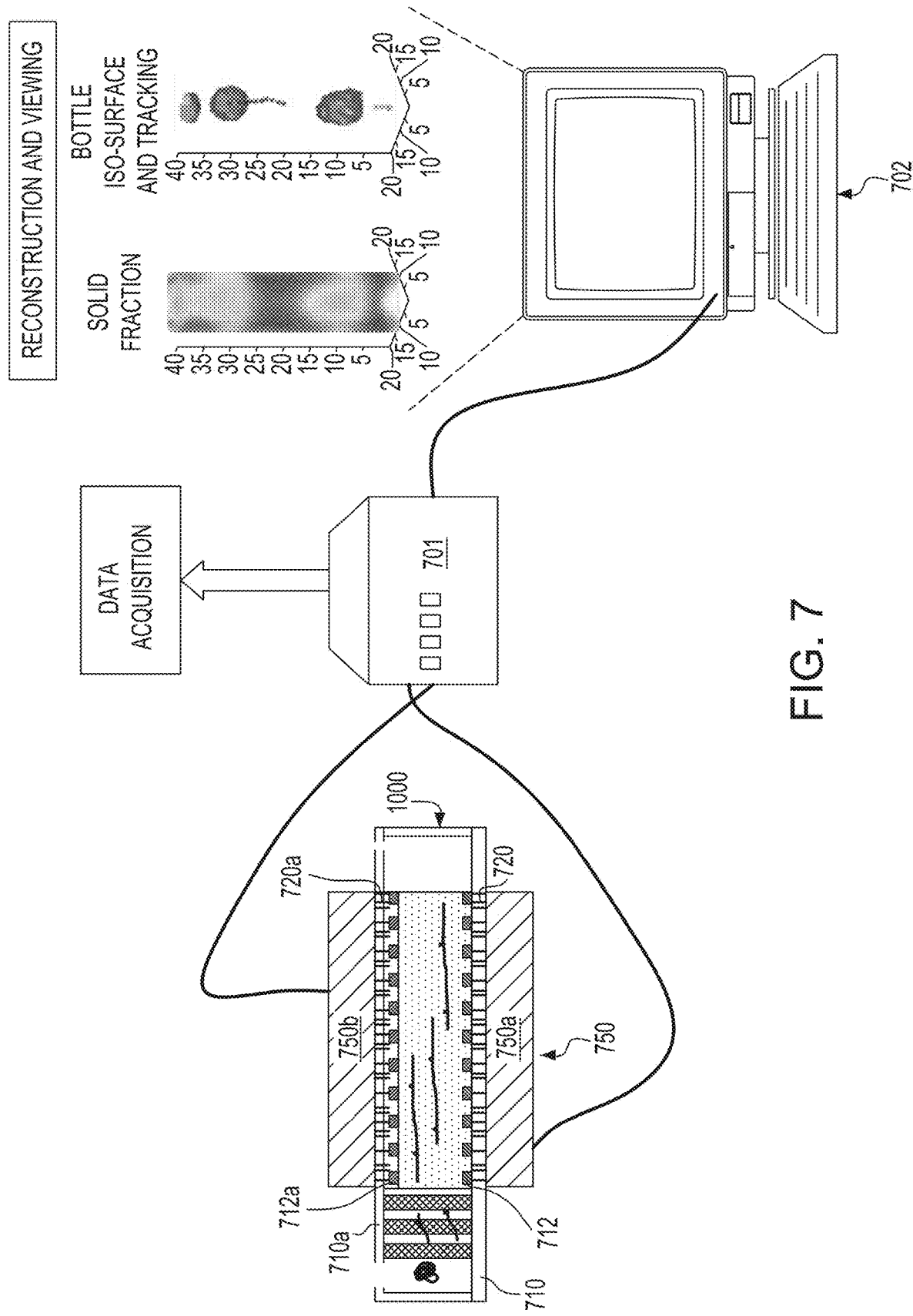
FIG. 7 is a system for sensing an analyte according to an embodiment of the present application employing an integrated sensing circuit.

Referring to FIG. 7, a system for sensing an analyte according to an embodiment of the present application is illustrated. The system includes a first exemplary micro-capacitive sensor array as illustrated, for example, in FIGS. 6A-6C, a data acquisition unit 701 connected to the micro-capacitive capacitive sensor array 1000 for data acquisition and a processor 702 connected to the data acquisition unit 701 for data processing and image generation.

In the embodiment and shown in FIG. 7, the data acquisition unit 701 is connected to the first substrate 710 and the second substrate 710a of the exemplary micro-capacitance sensor array of FIG. 6C 1000 through an integrated sensing circuit 750. The integrated sensing circuit 750 is capable of performing a time sequence of capacitance measurements to one electrode relative to all the other electrodes. The integrated sensing circuit 750 typically includes a plurality of subcircuits 750a, 750b that are bonded to the conductive circuit lines 720, 720a through I/O pins. The first conductive electrodes 712 and the second conductive electrodes 712a can thus be grouped in different fashions through the subcircuits 750a, 750b. When measuring the capacitance, the integrated sensing circuit 750 can provide an alternating current (AC) excitation or a direct current (DC) excitation. The DC excitation may include a path to ground (GND). The integrated sensing circuit 750 allows connecting first conductive electrodes 712 and the second conductive electrodes 712a with fewer leads, thus can improve signal-to-noise ratio, reduce the number of inputs/outputs and eliminate the need of using external circuitry for performing the same function.

As shown in FIG. 7, the integrated sensing circuit 750 includes a first subcircuit 750a bonded to a first set of conductive circuit lines 720 located at a first side of the first substrate 710 and a second subcircuit 750b bonded to a second set of conductive circuit lines 720a located at a first side of the second substrate 710a that is opposite from first set of conductive circuit lines 720. Such an arrangement allows independently acquiring signals from the subcircuits, which provides great flexibility in data acquisition. In this case and since the integrated sensing circuit 750 connects to the all of the conductive circuit lines 720/720a, the number of independent capacitance measurements available is the total number electrodes 712/712a.

Each subcircuit includes a pair of multiplexers coupled to an instrumentation amplifier. In one embodiment, the instrumentation amplifier may be a capacitance sense amplifier for AC or DC differential capacitance sensing or a two-lead (+/−) or a three-lead (+/−/ground) hook-up. In another embodiment, the instrumentation amplifier may be a current amplifier for quasi-static capacitance measurements or resistive measurement.

Scanning of capacitive sensor arrays of the present application is based on differential capacitance measurements of pairs of intersecting electrodes 112, 212. Since the first electrodes 112 and the second electrodes 212 are separated by the spacers 20 or gasket 20, the system of the present application allows image sensing across the first electrode plate 100 and the second electrode plate 200. In addition, by measuring differential capacitance among pairs of intersecting electrodes 112, 212 the effect of parasitic capacitance is eliminated.

While the present application has been particularly shown and described with respect to various embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A system for sensing an analyte comprising:
a micro-capacitive sensor array comprising:
at least one first conductive electrode located on, or embedded in, a first electrode plate;
at least one second conductive electrode located on, or embedded in, a second electrode plate, wherein said first electrode plate and said second electrode plate are overlapping and parallel, and wherein said first electrode plate and said second electrode plate are geographically separated forming at least one channel for sensing an analyte between said first electrode plate and said second electrode plate;
an integrated sensing circuit connected to each of said at least one first conductive electrodes of said first electrode plate and each of said at least one second conductive electrodes of said second electrode plate for performing sequential capacitance measurements through the channel; and
a processor connected to said integrated sensing circuit for constructing a movement image of an analyte.

2. The system of claim 1, wherein the integrated sensing circuit provides an alternating current (AC) excitation.

3. The system of claim 1, wherein the integrated sensing circuit provides a direct current (DC) excitation.

4. The system of claim 1, wherein said at least one first conductive electrode comprises a plurality of first conductive electrodes having a first polarity and said at least one second conductive electrode has a second polarity that is opposite of said first polarity.

5. The system of claim 4, wherein each of said plurality of first conductive electrodes are spaced apart or electrically isolated from one another.

6. The system of claim 5, wherein said micro-capacitive sensor array further comprises
a first substrate located on said first electrode plate;
a second substrate located on said second electrode plate; and
a first array of first vertical pillars on a portion of said first substrate adjacent to said at least one channel for sensing the analyte.

7. The system of claim 6, wherein each vertical pillar of said first array of vertical pillars has a first end contacting said first substrate and a second end contacting said second substrate.

8. The system of claim 7, further comprising a second array of vertical pillars on a second portion of said first substrate adjacent to said at least one channel for sensing the analyte, wherein said first array of vertical pillars and said second array of vertical pillars are on opposite ends of said at least one channel for sensing the analyte.

9. The system of claim 6, wherein said second substrate has an opening in a portion of said second substrate located adjacent to said at least one channel for sensing the analyte.

10. The system of claim 9, wherein said second substrate further has another opening in said second substrate located adjacent to the opposite end of said at least one channel for sensing the analyte.

11. The system of claim 1, further comprising an insulator layer on said at least one first conductive electrode of said first electrode plate.

12. The system of claim 11, further comprising another insulator layer on said at least one second conductive electrode of said second electrode plate.

13. The system of claim 1, further comprising a coating containing an antibody on said at least one first conductive electrode of said first electrode plate.

14. The system of claim 1, wherein said at least one channel for sensing an analyte comprises at least two nanochannels.

15. The system of claim 1, wherein the analyte is a nucleic acid.

* * * * *